United States Patent
Wan et al.

(10) Patent No.: US 12,303,475 B2
(45) Date of Patent: *May 20, 2025

(54) CONDITIONING IRRADIATED TISSUE FOR INCREASING VASCULARITY

(71) Applicant: The Board of Trustees of the Leland Stanford Junior University, Stanford, CA (US)

(72) Inventors: Derrick C. Wan, Stanford, CA (US); Geoffrey C. Gurtner, Portola Valley, CA (US); Michael T. Longaker, Atherton, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 454 days.

This patent is subject to a terminal disclaimer.

(21) Appl. No.: 17/721,125

(22) Filed: Apr. 14, 2022

(65) Prior Publication Data

US 2022/0241224 A1 Aug. 4, 2022

Related U.S. Application Data

(62) Division of application No. 16/642,467, filed as application No. PCT/US2018/050626 on Sep. 12, 2018, now Pat. No. 11,331,288.

(60) Provisional application No. 62/588,230, filed on Nov. 17, 2017, provisional application No. 62/558,698, filed on Sep. 14, 2017.

(51) Int. Cl.
*A61K 9/00* (2006.01)
*A61K 9/107* (2006.01)
*A61K 31/16* (2006.01)

(52) U.S. Cl.
CPC ............ *A61K 31/16* (2013.01); *A61K 9/0019* (2013.01); *A61K 9/1075* (2013.01)

(58) Field of Classification Search
CPC .... A61K 31/16; A61K 9/0019; A61K 9/1075; A61L 2300/412
See application file for complete search history.

(56) References Cited

U.S. PATENT DOCUMENTS 4,397,867 A 8/1983 Blake
4,760,051 A 7/1988 Pickart
(Continued)

FOREIGN PATENT DOCUMENTS

EP 1374868 A1 1/2004
JP H05-009114 A 1/1993
(Continued)

OTHER PUBLICATIONS

Flacco et al, Deferoxamine Conditioned of Irradiated Tissue Increases Fat Graft vol. Retention, Plast Reconstr Surg, Mar. 14(3): pp. 655-665. (Year: 2018).*
(Continued)

*Primary Examiner* — Carlos A Azpuru
(74) *Attorney, Agent, or Firm* — Travis G. Young; Bret E. Field; Bozicevic, Field & Francis LLP

(57) ABSTRACT

Methods of increasing perfusion and vascularity in irradiated tissue and of increasing retention of fat cells in a fat graft in irradiated tissue by applying an effective amount of DFO to the irradiated tissue at a treatment site. The DFO may be administered transdermally.

4 Claims, 10 Drawing Sheets

(56) References Cited

U.S. PATENT DOCUMENTS

| | | | |
|---|---|---|---|
| 4,877,770 | A | 10/1989 | Pickart |
| 4,992,445 | A | 2/1991 | Lawter et al. |
| 5,001,139 | A | 3/1991 | Lawter et al. |
| 5,023,252 | A | 6/1991 | Hseih |
| 5,047,427 | A | 9/1991 | Williamson |
| 5,382,574 | A | 1/1995 | Jorgensen |
| 5,676,968 | A | 10/1997 | Lipp et al. |
| 5,677,330 | A | 10/1997 | Abraham et al. |
| 6,117,437 | A | 9/2000 | Roreger |
| 6,156,334 | A | 12/2000 | Meyer-Ingold et al. |
| 6,337,350 | B1 | 1/2002 | Rahbar et al. |
| 6,348,465 | B1 | 2/2002 | Baker |
| 6,465,504 | B1 | 10/2002 | Lattmann et al. |
| 6,576,653 | B2 | 6/2003 | Du Bois |
| 6,579,544 | B1 | 6/2003 | Rosenberg et al. |
| 6,737,421 | B1 | 5/2004 | Lubish et al. |
| 6,984,636 | B2 | 1/2006 | Murphy et al. |
| 8,507,649 | B2 | 8/2013 | Lintner et al. |
| 10,098,857 | B2 | 10/2018 | Gurtner et al. |
| 10,751,304 | B2 | 8/2020 | Gurtner et al. |
| 11,331,288 | B2 * | 5/2022 | Wan ................ A61K 9/7023 |
| 2003/0060408 | A1 | 3/2003 | Bar-Or et al. |
| 2003/0082225 | A1 | 5/2003 | Mason |
| 2003/0086916 | A1 | 5/2003 | Goligorsky et al. |
| 2004/0059107 | A1 | 3/2004 | Malfroy-Camine et al. |
| 2004/0151765 | A1 | 8/2004 | Ritchie et al. |
| 2005/0215468 | A1 | 9/2005 | Bar-Or et al. |
| 2006/0100189 | A1 | 5/2006 | Gurtner et al. |
| 2006/0211746 | A1 | 9/2006 | Bergeron |
| 2006/0281748 | A1 | 12/2006 | Gurtner et al. |
| 2007/0104769 | A1 | 5/2007 | Feng et al. |
| 2007/0135369 | A1 | 6/2007 | Cooke et al. |
| 2009/0017439 | A1 | 1/2009 | Shimko et al. |
| 2009/0305963 | A1 | 12/2009 | Sukhatme et al. |
| 2010/0092546 | A1 | 4/2010 | Gurtner et al. |
| 2011/0159104 | A1 | 6/2011 | Teslenko |
| 2011/0212033 | A1 | 9/2011 | Tamarkin et al. |
| 2012/0207688 | A1 | 8/2012 | Guthery |
| 2012/0220651 | A1 | 8/2012 | Chevion et al. |
| 2013/0110132 | A1 | 5/2013 | Epstein et al. |
| 2014/0039069 | A1 | 2/2014 | Desai et al. |
| 2014/0364406 | A1 | 12/2014 | Gurtner et al. |
| 2014/0370078 | A1 | 12/2014 | Gurtner et al. |
| 2015/0174021 | A1 | 6/2015 | Campiche et al. |
| 2016/0039922 | A1 | 2/2016 | Attie |
| 2017/0296514 | A1 | 10/2017 | Miller et al. |
| 2018/0071265 | A1 | 3/2018 | Gurtner et al. |
| 2018/0193353 | A1 | 7/2018 | Gurtner et al. |
| 2020/0046653 | A1 | 2/2020 | Gurtner |
| 2020/0338024 | A1 | 10/2020 | Gurtner et al. |
| 2021/0113498 | A1 | 4/2021 | Gurtner |
| 2021/0315789 | A1 | 10/2021 | Gurtner |
| 2022/0016056 | A1 | 1/2022 | Gurtner et al. |

FOREIGN PATENT DOCUMENTS

| | | |
|---|---|---|
| JP | 10-120557 A | 5/1998 |
| WO | WO94/27594 A2 | 12/1994 |
| WO | WO00/19993 A2 | 4/2000 |
| WO | WO01/091774 A2 | 12/2001 |
| WO | WO02/098431 A1 | 12/2002 |
| WO | WO02/102345 A2 | 12/2002 |
| WO | WO03/049686 A2 | 6/2003 |
| WO | WO03/053997 A2 | 7/2003 |
| WO | WO2004/039430 A2 | 5/2004 |
| WO | WO2005/007192 A2 | 1/2005 |
| WO | WO2005/060986 A1 | 7/2005 |
| WO | WO2005/115379 A2 | 12/2005 |
| WO | WO2008/075207 A2 | 6/2008 |
| WO | WO2019/191309 A1 | 10/2019 |

OTHER PUBLICATIONS

Donneys et al., Localized Deferoxamine Injections Augment Vascularity and Improves Bony Union in Pathological Fracture Healing after Radiotherapy, Bone, Jan. 52(1): 318-325. (Year: 2013).*

Abaci et al., Effect of diabetes mellitus on formation of coronary collateral vessels; Circulation; 99(17); pp. 2239-2242; May 1999.

Abbott et al., The impact of diabetes on survival following myocardial infraction in men vs women. Framingham study; Jama; 260(23); pp. 3456-3460; Dec. 1988.

Adamis et al., Increased vascular endothelial growth factor levels in the vitreous of eyes with proliferative diabetic retinopathy; American Journal of Ophthalmology; 118(4); pp. 445-450; Oct. 1994.

Aiello et al., Role of vascular endothelial growth factor in diabetic vascular complications; Kidney International; 58(77); pp. S113-S119; Sep. 2000.

Aiello et al., Vascular endothelial growth factor in ocular fluid of patients with diabetic retinopathy and other retinal disorders; New England Journal of Medicine; 331(22); pp. 1480-1487; Dec. 1994.

Al-Mehdi et al., Depolarization-associated iron release with abrupt reduction in pulmonary endothelial shear stress in situ; Antioxidants and Redox Signaling; 2(2); pp. 335-345; Jun. 2000.

Altavilla et al., Inhibition of lipid peroxidation restores vascular endothelial growth factor expression and stimulates wound healing and angiogenesis in the genetically diabetic mouse; Diabetes; 50(3); pp. 667-674; Mar. 2001.

American Cancer Society, Cancer facts and figures 2017; 7 pages; retrieved from the internet (https://www.cancer.org/research/cancer-facts-statistics/all-cancer-facts-figures/cancer-facts-figures-2017.html) on Dec. 28, 2018.

American Society of Plastic Surgeons, Plastic surgery statistics report: 2017; 25 pages; retrieved from the internet (https://www.plasticsurgery.org/documents/News/Statistics/2017/plastic-surgery-statistics-full-report-2017.pdf) on Jan. 9, 2019.

Andrews, Disorders of iron metabolism; New England Journal of Medicine; 341(26); pp. 1986-1995; Dec. 23, 1999.

Arane-Conejo et al., Physiopathology of complications of diabetic foot; Gac. Med. Mex.; 193(3); pp. 255-264; (English Abstract) May-Jun. 2003.

Arora et al., Cutaneous microcirculation in the neuropathic diabetic foot improves significantly but not completely after successful lower extremity revascularization; Journal of vascular Surgery; 35(3); pp. 501-505; Mar. 2002.

Asahara et al., Bone marrow origin of endothelial progenitor cells responsible for postnatal vasculogenesis in physiological and pathological neovascularization; Circulation Research; 85(3); pp. 221-228; Aug. 6, 1999.

Asahara et al., Isolation of putative progenitor endothelial cells for angiogenesis; Science; 275(5302); pp. 964-966; Feb. 14, 1997.

Asahara et al., VEGF contributes to postnatal neovascularization by mobilizing bone marrow-derived endothelial progenitor cells; The EMBO Journal; 18(14); pp. 3964-3872; Jul. 15, 1999.

Barnett et al., Normal tissue reactions to radiotherapy: towards tailoring treatment dose by genotype; Nature Reviews Cancer; 9(2); pp. 134-142; 21 pages (Author Manuscript); Feb. 2009.

Bentzen, Preventing or reducing late side effects of radiation therapy: radiobiology meets molecular pathology; Nature Reviews Cancer; 6(9); pp. 702-713; Sep. 2006.

Bonham et al., Deferoxamine can prevent pressure ulcers and accelerate healing in aged mice; Wound Repair and Regeneration; 26(3); pp. 300-305; 14 pages, (Author Manuscript); May 2018.

Borelli et al., Transdermal Drug Delivery System for Deferoxamine Improves Vascular and Fat Graft Take Postirradiation; Plas Reconstr Surg Globe Open; 7(8 Suppl); pp. 131; 2019.

Bradley et al., Survival of diabetic patients after myocardial infarction; The American Journal of Medicine; 20(2); pp. 207-216; Feb. 1956.

Brem et al., Healing of elderly patients with diabetic foot ulcers, venous stasis ulcers, and pressure ulcers; Surgical Technology International; vol. 11; pp. 161-167; 2001.

Brown, Expression of vascular permeability factor (vascular endothelial growth factor) by epidermal keratinocytes during wound healing; Journal of Experimental Medicine; 176(5); pp. 1375-1379; Nov. 1992.

(56) References Cited

OTHER PUBLICATIONS

Brownlee, Biochemistry and molecular cell biology of diabetic complications; Nature; 414(6865); pp. 813-820; Dec. 2001.
Cameron et al., Neurovascular dysfunction in diabetic rats. Potential contribution of autoxidation and free radicals examined using transition metal chelating agents.; The Journal of Clinical Investigation; 96(2); pp. 1159-1163; Aug. 1995.
Carmeliet et al., Abnormal blood vessel development and lethality in embryos lacking a single VEGF allele; Nature; 380(6573); pp. 435-439; Apr. 4, 1996.
Caro et al., Lifetime costs of complications resulting from type 2 diabetes in the U.S.; Diabetes Care; 25(3); pp. 476-481; Mar. 2002.
Chang et al., Age decreases endothelial progenitor cell recruitment through decreases in hypoxia-induced factor 1 alpha stabilization during ischemia; Circulation; 116(24); pp. 2818-2829; Dec. 2007.
Chaston et al., Iron chelators for the treatment of iron overload disease: Relationship between structure, redox activity, and toxicity; America Journal of Hematology; 73(3); pp. 200-210; 22 pages, retrieved from the internet (https://onlinelibrary.wiley.com/doi/pdf/10.1002/ajh.10348); Jul. 2003.
Chatterjee et al., Inhibitors of poly (ADP-Ribose) synthetase protect rat proximal tubular cells against oxidant stress; Kidney International; 56(3); pp. 973-984; Sep. 1999.
Chekanov et al., Deferoxamine enhances neovascularization and recovery of ischemic skeletal muscle in an experimental sheep model; The Annals of Thoracic Surgery; 75(1); pp. 184-189; Jan. 2003.
Chilian et al., Microvascular occlusions promote coronary collateral growth; American Journal of Physiology-Heart and Circulatory Physiology; 258(4); pp. H1103-H1111; Apr. 1990.
Chou et al., Decreased cardiac expression of vascular endothelial growth factor and its receptors in insulin-resistant and diabetic states: A possible explanation for impaired collateral formation in cardiac tissue; Circulation; 105(3); pp. 373-379; Jan. 22, 2002.
Chung et al., Micro-computed tomography evaluation of human fat grafts in nude mice; Tissue Engineering Part C: Methods; 19(3); pp. 227-232; Jan. 4, 2013.
Church, Economic costs of diabetes in the U.S. in 2002; Diabetes Care; 26(3); pp. 917-932; Mar. 2003.
Clark et al., Soft-tissue reconstruction of the foot and ankle; The Orthopedic Clinics of North America; 24(3); pp. 489-503; Jul. 1993.
Crosby et al., Endothelial cells of hematopoietic origin make a significant contribution to adult blood vessel formation: Circulation Research; 87(9); pp. 728-730; Oct. 27, 2000.
Curio et al., Decreased cultured endothelial cell proliferation in high glucose medium is reversed by antioxidants: new insights on the pathophysiological mechanisms of diabetic vascular complications; In Vitro Cellular and Developmental Biology; 28(11/12); pp. 787-790; Nov. 1992.
Delay et al., Fat injection to the breast: technique results, and indications based on 880 procedures over 10 years; Aesthetic Surgery Journal; 29(5); pp. 360-376; Sep. 2009.
Diabetes Control and Complications Trial Research Grou, The effect of intensive treatment of diabetes on the development and progression of long-term complications in insulin-dependent diabetes mellitus; New England Journal of Medicine; 329(14); pp. 977-986; Sep. 30, 1993.
Donneys et al., Deferoxamine expedites consolidation during mandibular distraction osteogenesis; Bone; 55(2); pp. 384-390; 25 pages; (Author Manuscript); Aug. 2013.
Donneys et al., Localized deferoxamine injection augments vascularity and improves bony union in pathologic fracture healing after radiotherapy; Bone; 52(1); pp. 318-325; 23 pages (Author Manuscript); Jan. 2013.
Donneys et al., Deferoxamine restores callus size, mineralization, and mechanical strength in fracture healing after radiotherapy; Plastic and Reconstructive Surgery; 131(5); pp. 711e-719e; 13 pages (Author Manuscript); May 2013.
Dos Santos et al., Amphiphilic molecules in drug delivery systems; Drug Delivery Systems: Advanced Technologies Potentially Applicable in Personalized Treatment, Advances in Predictive, Preventive and Personalized Medicine 4, DOI 10.1007/978-94-007-6010-3_2; Springer Science + Business Media Dordrecht; pp. 35-85; (year of pub. sufficiently earlier than effective US filing date and any foreign priority date) 2013.
Du et al., Hyperglycemia inhibits endothelial nitric oxide synthase activity by posttranslational modification at the akt site; Journal of Clinical Investigation; 108(9); pp. 1341-1348; Nov. 2001.
Du et al., Insulin resistance causes proatherogenic changes in arterial endothelium by increasing fatty acid oxidation-induced superoxide production; The Journal of Clinical Investigation; 116(4); pp. 1071-1080; Apr. 3, 2006.
Duscher et al., Comparison of the hydroxylase inhibitor dimethyloxalylglycine and the iron chelator deferoxamine in diabetic and aged wound healing; Plastic and Reconstructive Surgery; 139(3); pp. 695e-706e; 18 pages, (Author Manuscript); Mar. 2017.
Duscher et al., Fibroblast-specific deletion of hypoxia inducible factor-1 critically impairs murine cutaneous neovascularization and wound healing; Plastic and Reconstructive Surgery; 136(5); pp. 1004-1013; 15 pages, (Author Manuscript); Nov. 2015.
Duscher et al., Transdermal deferoxamine prevents pressure-induced diabetic ulcers; Proceedings of the National Academy of Sciences; 112(1); pp. 94-99; 6 pages; (Author Manuscript); Jan. 6, 2015.
Eto et al., The fate of adipocytes after nonvascularized fat grafting: evidence of early death and replacement of adipocytes; Plastic and Reconstructive Surgery; 129(5); pp. 1081-1092; May 2012.
Farberg et al., Deferoxamine enhances bone regeneration in mandibular distraction osteogenesis; Plastic and Reconstructive Surgery; 133(3); pp. 666-671; 11 pages (Author Manuscript); Mar. 2014.
Felice et al., Deferoxamine administration delivers translational optimization of distraction osteogenesis in the irradiated mandible; Plastic and Reconstructive Surgery; 132(4); pp. 542e-548e; 11 pages (Author Manuscript); Oct. 2013.
Fernandez-Real et al., Cross-talk between iron metabolism and diabetes; Diabetes; 51(8); pp. 2348-2354; Aug. 2002.
Ferrara et al., The biology of VEGF and its receptors; Nature Medicine; 9(6); pp. 669-676; Jun. 2003.
Flacco et al., Deferoxamine preconditioning of irradiated tissue improves perfusion and fat graft retention; Plastic Reconstructive Surgery; 141(3); pp. 655-665; 17 pages; (Author Manuscript); Mar. 2018.
Forsythe et al., Activation of vascular endothelial growth factor, gene transcription by hypoxia-inducible factor 1; Molecular and Cellular Biology; 16(9); pp. 4604-4613; Sep. 1996.
Fraga et al., Iron toxicity and antioxidant nutrients; Toxicology; 180(1); pp. 23-32; Oct. 2002.
Frank et al., Regulation of vascular endothelial growth factor expression in cultured keratinocytes. Implications for normal and impaired wound healing; Journal of Biological Chemistry; 270(21); pp. 12607-12613; May 26, 1995.
Fujiwara et al., Extracellular superoxide dismutase deficiency impairs wound healing in advanced age by reducing neovascularization and fibroblast function; Experimental Dermatology; 25(3); pp. 206-211; 14 pages, (Author Manuscript); Mar. 2016.
Galiano et al., Quantitative and reproducible murine model of excisional wound healing; Wound Repair and Regeneration; 12(4); pp. 485-492; Aug. 2004.
Garcia et al., Morbidity and mortality in diabetes in the Framingham population. Sixteen year follow-up study; Diabetes; 23(2); pp. 105-111; Feb. 1974.
Garza et al., Studies in fat grafting: Part III. Fat grafting irradiated tissue-improved skin quality and decreased fat graft retention; Plastic and Reconstructive Surgery; 134(2); pp. 249-257; 15 pages; (Author Manuscript); Aug. 2014.
Gaynes et al., National Nosocomial Infections Surveillance System; plans for the 1990s and beyond; Am J Med; 91(3) Suppl 2; pp. S116-S120; Sep. 16, 1991.
Giardino et al., BCL-2 expression or antioxidants prevent hyperglycemia-induced formation of intracellular advanced glycation end products in bovine endothelial cells; The Journal of Clinical Investigation; 97(6); pp. 1422-1428; Mar. 15, 1996.

(56) References Cited

OTHER PUBLICATIONS

Gill et al., Vascular trauma induces rapid but transient mobilization of VEGFR2(+)AC133 (+) endothelial precursor cells; Circulation Research; 88(2); pp. 167-174; Feb. 2001.

Gkouvatsos et al., Regulation of iron transport and the role of transferrin; Biochimica et Biophysica Acta (BBA)—General Subjects; 1820(3); pp. 188-202; Mar. 2012.

Goova et al., Blockade of receptor for advanced glycation end-products restores effective wound healing in diabetic mice; The American Journal of Pathology; 159(2); pp. 513-525; Aug. 2001.

Grundy, Cardiovascular and Metabolic risk factors: How can we improve outcomes in the high-risk patient?; The American Journal of Medicine; 120(9); pp. S3-S8; Sep. 2007.

Guzik et al., Mechanisms of increased vascular superoxide production in human diabetes mellitus: Role of NAD(P)H oxidase and endothelial nitric oxide synthase; Circulation; 105(14); pp. 1656-1662; Apr. 2002.

Haffner et al., Mortality from coronary heart disease in subjects with type 2 diabetes and in nondiabetic subjects with and without prior myocardial infarction; New England Journal of Medicine; 339(4); pp. 229-234; Jul. 23, 1998.

Haffner, Abdominal adiposity and cardiometabolic risk: Do we have all the answers?; The American Journal of Medicine; 120(9); pp. S10-S16; Sep. 2007.

Hammes et al., Benfotiamine blocks three major pathways of hyperglycemic damage and prevents experimental diabetic retinopathy; Nature Medicine; 9(3); pp. 294-299; Mar. 2003.

Harris et al., Prevalence of diabetes, impaired fasting glucose, and impaired glucose tolerance in U.S. adults. The third national health and nutrition examination survey, 1988-1994; Diabetes Care; 21(4); pp. 518-524; Apr. 1998.

Harrop et al., Contributing factors to surgical site infections; JAAOS—J Am Acad Orthop Surg; 20(2); pp. 94-101; Feb. 1, 2012.

Hartzen et al., The antibacterial activity of a siderophore: 3. The activity of deferoxamine in vitro and its influence on the effect of antibiotics against *E coli*, P mirabilis and coagulase-negative staphylococci; APMIS; 102(1-6); pp. 219-226; Jan. 1994.

Hattori et al., Deferoxamine improves coronary vascular responses to sympathetic stimulation in patients with type 1 diabetes mellitus; European journal of Nuclear Medicine and Molecular Imaging; 29(7); pp. 891-898; Jul. 2002.

Hattori et al., Vascular endothelial growth factor and angiopoietin-1 stimulate postnatal hematopoiesis by recruitment of vasculogenic and hematopoietic stem cells; Journal of Experimental Medicine; 193(9); pp. 1005-1014; May 2001.

Hegedus et al., Radiation dermatitis: an overview; Int. J. Dermatol.; 56(9); pp. 909-914; Sep. 2017.

Helfant et al., Functional importance of the human coronary collateral circulation; New England Journal of Medicine; 284(23); pp. 1277-1281; Jun. 10, 1971.

Hershko et al., ICL670A: a new synthetic oral chelator: evaluation in hyper transfused rats with selective radioiron probes of hepatocellular and reticuloendothelial iron stores and in iron-loaded rat heart cells in culture; Blood; 97(4); pp. 1115-1122; Feb. 2001.

Hiller et al., Diabetic retinopathy and cardiovascular disease in type II diabetics. The Framingham study and the Framingham eye study; American Journal of Epidemiology; 128(2); pp. 402-409; Aug. 1988.

Howard et al., Prevention conference VI: Diabetes and cardiovascular disease: Writing group I: Epidemiology; Circulation; 105(18); pp. e132-137; 6 pages; (Author Manuscript); May 2002.

Hymes et al., Radiation dermatitis: clinical presentation, pathophysiology, and treatment; Journal of the American Academy of Dermatology; 54(1); pp. 28-46; Jan. 2006.

Ihnat et al., Solution equilibria of deferoxamine amides; Journal of Pharmaceutical Sciences; 91(7); pp. 1733-1741; Jul. 2002.

Isner et al., Angiogenesis and vasculogenesis as therapeutic strategies for postnatal neovascularization; The Journal of Clinical Investigation; 103(9); pp. 1231-1236; May 1999.

Iyer et al., Cellular and developmental control of O2 homeostasis by hypoxia-inducible factor 1 alpha; Genes and Development; 12(2); pp. 146-162; Jan. 15, 1998.

Jacobson et al., Vessel-depleted neck: techniques for achieving microvascular reconstruction; Head and Neck: Journal for the Sciences and Specialties of the Head and Neck; 30(2); pp. 201-207; Feb. 2008.

Jude et al., Peripheral arterial disease in diabetic and nondiabetic patients: a comparison of severity and outcome; Diabetes Care; 24(8); pp. 1433-1437; Aug. 2001.

Kalka et al., Vascular endothelial growth factor (165) gene transfer augments circulating endothelial progenitor cells in human subjects; Circulation Research; 86(12); pp. 1198-1202; Jun. 2000.

Kannel et al., Diabetes and cardiovascular risk factors: the Framingham study; Circulation; 59(1); pp. 8-13; Jan. 1979.

Kip et al., Coronary angioplasty in diabetic patients. The national heart, lung, and blood institute percutaneous transluminal coronary angioplasty registry; Circulation; 94(8); pp. 1818-1825; (Author Manuscript) Oct. 1996.

Kip et al., Differential influence of diabetes mellitus on increased jeopardized myocardium after initial angioplasty or bypass surgery: Bypass angioplasty revascularization investigation; Circulation; 105(16); pp. 1914-1920; Apr. 23, 2002.

Kipshidze et al., Therapeutic angiogenesis for patients with limb ischemia by utilization of fibrin meshwork. Pilot randomized controlled study; International Angiology; 1(4); pp. 349-355; 8 pages, (Author Manuscript); Dec. 2003.

Kontoghiorghes et al., The design and development of deferiprone (L1) and other iron chelators for clinical use: targeting methods and application prospects; Current Medicinal Chemistry; 11(16); pp. 2161-2183; Aug. 2004.

Kreilgaard, Influence of microemulsions on cutaneous drug delivery. Advanced drug delivery reviews; 54(1); pp. S77-98; Nov. 1, 2002.

Kress et al., The relationship between intracellular free iron and cell injury in cultured neurons, astrocytes, and oligodendrocytes; Journal of Neuroscience; 22(14); pp. 5848-5855; Jul. 15, 2002.

Lawrence et al., Microemulsion-based media as novel drug delivery systems; Advanced Drug Delivery Reviews; 64; pp. 175-193; Sep. 13, 2012.

Lee et al., Hypoxia-inducible factor (HIF-1alpha): its protein stability and biological functions; Exp Mol Med; 36(1); pp. 1-12; Feb. 2004.

Lerman et al., Cellular dysfunction in the diabetic fibroblast: Impairment in migration, vascular endothelial growth factor production and response to hypoxia; The American Journal of Pathology; 162(1); pp. 303-312; Jan. 2003.

Lim et al., Autologous fat transplantation in the craniofacial patient: the UCLA experience; The Journal of Craniofacial Surgery; 23(4); pp. 1061-1066; Jul. 2012.

Luan et al., Cell-assisted lipotransfer improves volume retention in irradiated recipient sites and rescues radiation-induced skin changes; Stem Cells; 34(3); pp. 668-673; Mar. 2016.

Lukanov et al., Molecular thermodynamic modeling of reverse micelles and water-in-oil microemulsions; Langmuir; 32(13); pp. 3100-3109; Mar. 25, 2016.

Mann et al., Management of acute iron overdose; Clinical Pharmacy; 8(6); pp. 428-440; (Abstract Only) Jun. 1989.

Margolis et al., Risk factors for delayed healing of neuropathic diabetic foot ulcers: A pooled analysis; Archives of dermatology; 136(12); pp. 1531-1535; Dec. 2000.

Marsh et al., Hypoxic induction of vascular endothelial growth factor is marked decreased in diabetic individuals who do not develop retinopathy; Diabetes Care; 23(9); pp. 1375-1380; Sep. 2000.

Meijler et al., Synthesis and evaluation of iron chelators with masked hydrophilic moieties; Journal of the American Chemical Society; 124(43); pp. 12666-12667; Oct. 30, 2002.

Mericli et al., Deferoxamine mitigates radiation-induced tissue injury in a rat irradiated TRAM flap model; Plastic and reconstructive surgery; 135(1); pp. 124e-134e; Jan. 2015.

(56) References Cited

OTHER PUBLICATIONS

Minniti et al., Leg Ulcers in sickle cell disease; America Journal of Hematology; 85(10); pp. 831-833; 10 pages (Author Manuscript); Oct. 2010.

Momeni et al., Clinical use of deferoxamine in distraction osteogenesis of irradiated bone; The Journal of Craniofacial Surgery; 27(4); pp. 880-882; 10 pages (Author Manuscript); Jun. 2016.

Moreau-Marquis et al., Tobramycin and FDA-approved iron chelators eliminate *Pseudomonas aeruginosa* biofilms on cystic fibrosis cells; Am J Respir Cell Mol Biol; 41(3); pp. 305-313; Sep. 2009.

Moreno-Navarrete et al., Fine-tuned iron availability is essential to achieve optimal adipocyte differentiation and mitochondrial biogenesis; Diabetologia; 57(9); pp. 1957-1967; Sep. 2014.

Muha, Local wound care in diabetic food complications. Aggressive risk management and ulcer treatment to avoid amputation; Postgraduate Medicine; 106(1); pp. 97-102; Jul. 1999.

Mulder et al., Enhanced healing of ulcers in patients with diabetes by topical treatment with glycyl-l-histidyl-l-lysine copper; Wound Repair and Regeneration; 2(4); pp. 259-269; Oct. 1994.

Nagai et al., Involvement of Endocytosis in the Transdermal Penetration Mechanism of Ketoprofen Nanoparticles; Int J. Mol. Sci.; 19(2138), pp. 1-13; 2018.

Nagler et al., Novel protection strategy against x-ray-induced damage to salivary glands; Radiation Research Society; 149(3); pp. 271-276; Mar. 1998.

Narang et al., Stable drug encapsulation in micelles and microemulsions: Intl. Journal of Pharmaceutics; 345(1-2); pp. 9-25; Sep. 8, 2007.

National Cancer Institute, Head and neck cancers; 11 pages; retrieved from the internet (https://www.cancer.gov/types/head-and-neck/head-neck-fact-sheet) on Jan. 9, 2019.

Nishikawa et al., Normalizing mitochondrial superoxide production blocks three pathways of hyperglycemic damage; Nature; 404(6779); pp. 787-790; Apr. 2000.

Nissen et al., Vascular endothelial growth factor mediates angiogenic activity during the proliferative phase of wound healing; The American Journal of Pathology; 152(6); pp. 1445-1452; Jun. 1998.

Novartis Pharmaceuticals Corporation, Desferal deferoxamine mesylate for injection USP vials Rx only prescribing information; 8 pages; retrieved from the internet (https://www.pharma.us.novartis.com/sites/www.pharma.us.novartis.com/files/desferal.pdf) on Oct. 21, 2019.

Obrosova et al., Aldose reductase inhibitor siderostat prevents retinal oxidative stress and vascular endothelial growth factor overexpression in streptozotocin-diabetic rats; Diabetes; 52(3); pp. 864-871; Mar. 2003.

Ozer, The role of iron on breast cancer stem-like cells; Cellular and Molecular Biology; 62(4); pp. 25-30; Apr. 30, 2016.

Palumbo et al., Diabetes mellitus: Incidence, prevalence, survivorship, and causes of death in Rochester, Minnesota, 1945-1970; Diabetes; 25(7); pp. 566-573; Jul. 1976.

Partamian et al., Acute myocardial infarction in 258 cases of diabetes. Immediate mortality and five-year survival; New England Journal of Medicine; 273(9); pp. 455-461; Aug. 26, 1965.

Pedchenko et al., Deferoxamine suppresses experimental allergic encephalomyelitis induced by MBP in SJL mice; Journal of Neuroimmunology; 84(2); pp. 188-197; Apr. 1998.

Pelosi et al., Identification of the hemangioblast in postnatal life; Blood; 100(9); pp. 3203-3208; Nov. 2002.

Peters et al., Vascular endothelial growth factor receptor expression during embryogenesis and tissue repair suggests a role in endothelial differentiation and blood vessel growth; Proceedings of the National Academy of Sciences; 90(19); pp. 8915-8919; Oct. 1993.

Pochon et al., A novel derivative of the chelon deferoxamine for site-specific conjugation to antibodies; International Journal of Cancer; 43(6); pp. 1188-1194; Jun. 1989.

Price et al., Chelating activity of advanced glycation end-product inhibitors; Journal of Biological Chemistry; 276(52); pp. 48967-48972; Dec. 2001.

Rennert et al., Diabetes impairs the angiogenic potential of adipose-derived stem cells by selectively depleting cellular subpopulations; Stem Cell Research and Therapy; 5(3):79; doi:10.1186/scrt468; 12 pages; Sep. 2014.

Ress et al., Free radical damage in acute nerve compression; Annals of Plastic Surgery; 34(4); pp. 388-395; Apr. 1995.

Richard et al., p42/p44 mitogen-activated protein kinases phosphorylate hypoxia-inducible factor 1 alpha (HIF-1 alpha) and enhance the transcriptional activity of HIF-1; Journal of Biological Chemistry; 274(46); pp. 32631-32637; Nov. 12, 1999.

Rivard et al., Rescue of diabetes-related impairment of angiogenesis by intramuscular gene therapy with adeno-VEGF; American Journal of Pathology; 154(2); pp. 355-363; Feb. 1999.

Rose et al., Deferoxamine stability in intravenous solution; Annal of the New York Academy of Sciences; 850; pp. 488-489; Jun. 1998.

Ryan, Ionizing radiation: the good, the bad, the bad, and the ugly; Journal of Investigative Dermatology; 132(3); pp. 985-993; Mar. 2012.

Salvemini et al., Superoxide dismutase mimetics; Pulmonary Pharmacology and Therapeutics; 15(5); pp. 439-447; Oct. 2002.

Sang et al., MAPK signaling up-regulates the activity of hypoxia-inducible factors by its effects on p300; Journal of Biological Chemistry; 278(16); pp. 14013-14019; Apr. 18, 2003.

Schatteman et al., Blood derived angioblasts accelerate blood-flow restoration in diabetic mice; The Journal of Clinical Investigation; 106(4); pp. 571-578; Aug. 2000.

Schratzberger et al., Reversal of experimental diabetic neuropathy by VEGF gene transfer; The Journal of Clinical Investigation; 107(9); pp. 1083-1092; May 2001.

Schwartz et al., Coronary bypass graft patency in patients with diabetes in the bypass angioplasty revascularization investigation (BART); Circulation; 106(21); pp. 2652-2658; Nov. 19, 2002.

Semenza et al., A nuclear factor induced by hypoxia via de novo protein synthesis blinds to the human erythropoietin gene enhancer at a site required for transcriptional activation; Molecular and Cellular Biology; 12 (12); pp. 5447-5454; Dec. 1992.

Semenza et al., Hypoxia-Inducible nuclear factors bind to an enhancer element located 3' to the human erythropoietin gene; National Academy of Sciences; 88(13); pp. 5680-5684; Jul. 1991.

Shi et al., Evidence for circulating bone marrow-derived endothelial cells; Blood; 92(2); pp. 362-367; Jul. 1998.

Shweiki et al., Vascular endothelial growth factor induced by hypoxia may mediate hypoxia-initiated angiogenesis; Nature; 359(6398); pp. 843-845; Oct. 1992.

Siebert et al., The inframammary extended circumflex scapular flap: an aesthetic improvement of the parascapular flap; Plastic and Reconstructive Surgery; 99(1); pp. 70-77; Jan. 1997.

Silhi, Diabetes and wound healing; Journal of Wound Care; 7(1); pp. 47-51; Jan. 1998.

Simovic et al., Improvement in chronic ischemic neuropathy after intramuscular phVEGF165 gene transfer in patients with critical limb ischemia; Archives of Neurology; 58(5); pp. 761-768; May 2001.

Soutoglou et al., Acetylation regulates transcription factor at multiple levels; Molecular Cell; 5(4); pp. 745-751; Apr. 2000.

Spear et al., Fat injection to correct contour deformities in the reconstructed breast; Plastic and Reconstructive Surgery; 116(5); pp. 1300-1305; Oct. 2005.

Stadler et al., Development of a simple, noninvasive, clinically relevant model of pressure ulcers in the mouse; J Invest Surg; 17(4); pp. 221-227; Jan. 1, 2004.

Suga et al., Adipose tissue remodeling under ischemia: death of adipocytes and activation of stem/progenitor cells; Plastic and Reconstructive Surgery; 126(6); pp. 1911-1923; Dec. 2010.

Takahashi et al., Ischemia and cytokine-induced mobilization of bone marrow-derived endothelial progenitor cells for neovascularization; Nature Medicine; 5(4); pp. 434-438; Apr. 1999.

Talegaonkar et al., Microemulsions: A novel approach to enhanced drug delivery; Recent patents on drug delivery and formulation; 2(3); pp. 238-257; Nov. 2008.

Taniyama et al., Therapeutic angiogenesis induced by human hepatocyte growth factor gene in rat diabetic hind limb ischemia model:

(56) References Cited

OTHER PUBLICATIONS

Molecular mechanisms of delayed angiogenesis in diabetes; Circulation; 104(19); pp. 2344-2350; Nov. 2001.
Tchanque-Fossuo et al., Deferoxamine: potential novel topical therapeutic for chronic wounds; British Journal of Dermatology; 176(4); pp. 1056-1059; Apr. 2017.
Temiz et al., Effects of deferoxamine on fat graft survival; Facial Plastic Surgery; 32(04); pp. 438-443; Aug. 2016.
Tepper et al., Human endothelial progenitor cells from type II diabetes exhibit impaired proliferation, adhesion, and incorporation into vascular structures; Circulation; 106(22); pp. 2781-2786; Nov. 26, 2002.
Thangarajah et al., HIF-1alpha dysfunction in diabetes; Cell Cycle; 9(1); pp. 75-79; Jan. 2010.
Thangarajah et al., The molecular basis for impaired hypoxia-induced VEGF expression in diabetic tissues; Proceedings of the National Academy of Sciences; 106; pp. 13505-13510; doi:10.1073/pnas.0906670106; 6 pages; Jul. 27, 2009.
Tooke, Microvasculature in diabetes; Cardiovascular Research; 32(4); pp. 764-771; Oct. 1996.
Torti et al., Iron and cancer: more ore to be mined; Nature Reviews Cancer; 13(5); pp. 342-355; 33 pages (Author Manuscript); May 2013.
Trivedi et al.; Nanomicellar formulation for sustained drug delivery: strategies and underlying principles; Nanomedicine (Lond); 5(3); pp. 485-505; Apr. 2010.
Tuomilehto et al., Diabetes mellitus as a risk factor for death from stroke. Prospective study of the middle-aged Finnish population; Stroke; 27(2); pp. 210-215; (Author Manuscript) Feb. 1996.
Uemura et al., Diabetes mellitus enhances vascular matrix metalloproteinase activity: Role of oxidative stress; Circulation Research; 88(12); pp. 1291-1298; Jun. 22, 2001.
Uusitupa et al., 5-Year incidence of atherosclerotic vascular disease in relation to general risk factors, insulin level, and abnormalities in lipoprotein composition in non-insulin-dependent diabetic and nondiabetic patients; Circulation; 82(1); pp. 27-36; Jul. 1990.
Van Asbeck et al., Inhibition of bacterial multiplication by the iron chelator deferoxamine: potentiating effect of ascorbic acid; Eur J. Clin Microbiol; 2(5); pp. 426-431; Oct. 1, 1983.
Van Asbeck et al., Synergy between the iron chelator deferoxamine and the antimicrobial agents gentamicin, chloramphenicol, cefalothin, cefotiam and cefsulodin; Eur J Clin Microbiol; 2(5); pp. 432-438; Oct. 1, 1983.
Vrignaud et al., Reverse micelle-loaded lipid nanocarriers: a novel drug delivery system for the sustained release of doxorubicin hydrochloride; European Journal of Pharmaceutics and Biopharmaceutics; 79(1); pp. 197-204; Sep. 2011.
Wakisaka et al., Epstein-Barr virus latent membrane protein 1 induces synthesis of hypoxia-inducible factor 1alpha; Mol Cell Biol; 24(12); pp. 5223-5234; Jun. 15, 2004.
Waltenberger, Impaired collateral vessel development in diabetes: Potential cellular mechanisms and therapeutic implications; Cardiovascular Research; 49(3); pp. 554-560; Feb. 2001.
Wang et al., Local injection of deferoxamine improves neovascularization in ischemic diabetic random flap by increasing HIF-1 alpha and VEGF expression; Plos one; 9(6); e100818; 8 pages; Jun. 25, 2014.
Weinstein et al., Deferoxamine decreases necrosis in dorsally based pig skin flaps; Otolaryngology—Head and Neck Surgery: Official Journal of American Academy of Otolaryngology-Head and Neck Surgery; 101(5); pp. 559-561; Nov. 1989.
Weng et al., Mimic hypoxia improves angiogenesis in ischemic random flaps; Journal of Plastic, Reconstructive and Aesthetic Surgery; 63(12); pp. 2152-2159; Dec. 2010.
Wilson, Diabetes mellitus and coronary heart disease; American Journal of Kidney Diseases; 32(5); pp. S89-S100; Nov. 1998.
Wong et al., Microvascular reconstruction in the vessel-depleted neck; Current Opinion in Otolaryngology and Head and Neck Surgery; 18(4); pp. 223-226; Aug. 2010.
Yamasaki et al., Deferoxamine for advanced hepatocellular carcinoma; New England Journal of Medicine; 365(6); pp. 576-578; Aug. 11, 2011.
Yarnold et al., Pathogenetic mechanisms in radiation fibrosis; Radiotherapy and Oncology; 97(1); pp. 149-161; Oct. 2010.
Yarom et al., Human coronary microvessels in diabetes and ischemia morphometric study of autopsy material; Journal of Pathology; 166(3); pp. 265-270; Mar. 1992.
Yu et al., Iron chelators for the treatment of cancer; Current Medicinal Chemistry; 19(17); pp. 2689-2702; Jun. 2012.
Zanger et al., CREB binding protein recruitment to the transcription complex requires growth factor-dependent phosphorylation of ites GF box; Molecular Cell; 7(3); pp. 551-558; Mar. 2001.
Zhan et al., Excess length of stay, charges, and mortality attributable to medical injuries during hospitalization; 290(14); pp. 1868-1874; Oct. 8, 2003.
Zimmet et al., Global and societal implications of the diabetes epidemic; Nature; 414(6865); pp. 782-787; Dec. 2001.
Zuanetti et al., Influence of diabetes on mortality in acute myocardial infarction: Data from the GISSI-2 study; American College of Cardiology; 22(7); pp. 1788-1794; Dec. 1993.

\* cited by examiner

DFO Treated

Saline Treated

CONDITIONING IRRADIATED TISSUE FOR INCREASING VASCULARITY

CROSS REFERENCE TO RELATED APPLICATIONS

This application is a division of U.S. application Ser. No. 16/642,467, filed Feb. 27, 2020, which application is a U.S. National Stage Application of PCT Application No. PCT/US2018/050626 filed Sep. 12, 2018, which application claims the benefit of U.S. Application No. 62/558,698, filed Sep. 14, 2017, and U.S. Application No. 62/588,230, filed Nov. 17, 2017, each of which is herein incorporated by reference in its entirety.

STATEMENT AS TO FEDERALLY SPONSORED RESEARCH

This invention was made with Government support under Grant Nos. DE021683, DE025597, DE026914 and DE024269 awarded by the National Institutes of Health. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

After heart disease, cancer remains the leading cause of death in the United States, with an estimated 1.6 million new cancer cases diagnosed and 600,000 cancer-related deaths projected for 2017. However, in recent years, substantial progress in medical care has been made, with surgery, chemotherapy, and radiation therapy increasing both the number of cancer survivors and the length of their survival. With this improvement, long-term issues related to treatment of cancer, such as with radiation therapy, have become increasingly apparent, and have been shown to profoundly impact quality of life. Radiation-induced soft tissue injury is one of the most common side effects of radiotherapy, affecting over 90% of patients, and the resulting soft tissue atrophy and fibrosis can lead to both severe cosmetic and long-term functional impairment.

Radiation therapy is a mainstay in the treatment of many malignancies. Radiation therapy can cause collateral damage to surrounding tissue, however, with resultant hypovascularity, fibrosis, and atrophy, and the damaged tissue can be difficult to reconstruct. Fat grafting has been shown to improve the quality of irradiated skin, but volume retention of the grafted fat cells is significantly decreased.

Chronic radiation injury is characterized by epidermal thinning, eosinophilic homogenized sclerosis of dermal collagen, scattered large and atypical fibroblasts, and fibrous thickening with luminal obliteration of deep vessels. Vascular damage and development of fibrosis is thought to result from radiation-induced cytokine expression, generation of reactive oxygen species, and cellular apoptosis, and soft tissue reconstruction of such hostile sites remains extremely challenging. While autologous fat grafting has become increasingly popular to address post-radiation soft tissue deficits, fibroinflammatory changes and hypovascularity have been associated with poorer fat graft outcomes. Improved retention has been noted with cell assisted lipotransfer, but the functional heterogeneity among stromal cells used to enrich lipoaspirate, in concert with concerns regarding post-oncologic locoregional recurrence, has limited the wide-spread adoption of this strategy.

Over 5.6 million soft tissue reconstructive procedures are performed annually in the United States, with the majority related to tumor extirpation and sequelae of adjuvant radiation therapy. Even with intact overlying epithelium, insufficient underlying soft tissue results in visible asymmetry and contour abnormalities, and may also contribute to unstable wounds and inadequate protection of critical organs and structures including bone, implanted hardware, and large vessels. While radiation therapy has been shown to be incredibly effective at reducing local recurrence risk for various tumors, collateral damage to adjacent soft tissue resulting in obliteration of microvasculature and fibrosis may significantly complicate reconstructive strategies.

Autologous fat grafting has emerged as an increasingly popular strategy to manage soft tissue deficiencies throughout the body, and this technique has been applied clinically to reconstruct defects secondary to cancer resection. However, transfer of avascular fat to irradiated sites remains challenging, as radiation induced changes to the recipient bed (i.e., hypovascularity) result in poorer fat graft survival. Cell-based strategies to enhance volume retention, through enrichment of fat grafts with additional adipose-derived stromal cells, have been shown to improve outcomes, but translation of this approach remains difficult due to known heterogeneity of the stromal vascular fraction and regulatory hurdles.

Deferoxamine (DFO) is an FDA-approved iron chelating medication for acute iron intoxication and chronic iron overload that has also been shown to increase angiogenesis. DFO has been demonstrated to increase hypoxia-inducible factor-1 alpha (HIF-1$\alpha$) activity and enhance expression of angiogenic growth factors. Studies have also shown local injection of DFO to improve ischemic flap survival in both mouse and pig models, with increased skin flap blood perfusion and capillary density noted in DFO-treated animals. Furthermore, in the setting of irradiated bone, multiple reports have found DFO to promote bone regeneration following distraction osteogenesis through enhanced vascularity.

The potential of DFO as an angiogenic and antioxidant agent with the potential to improve fat graft survival in healthy subjects has also been studied, and its use to increase the viability of fat grafts for plastic surgery has been proposed. Importantly, DFO was recently suggested to promote fat graft viability in a rat model. Temiz and colleagues described serial injections of 300 mg DFO into inguinal fat pads transplanted to parascapular subcutaneous pockets, which resulted in significantly greater weight measurements after two months. However, more inflammation and fibrosis was noted in DFO injected fat grafts, though no change in cellular apoptosis was appreciated. Repeated manipulation of fat grafts with each injection may have contributed to this observation. In addition, adipogenic differentiation of resident stromal cells has been purported to contribute to long-term fat graft retention, and direct exposure of DFO to fat grafts may be detrimental to this process. Studies have shown intracellular iron deficiency through DFO administration to severely blunt adipocyte differentiation. These findings thus temper enthusiasm for direct injection of DFO into fat grafts.

SUMMARY OF THE DISCLOSURE

One aspect of the invention provides a method of increasing retention of fat cells in a fat graft in irradiated tissue. In some embodiments, the method includes the steps of applying an effective amount of DFO to the irradiated tissue at a treatment site; and increasing retention of fat cells in the fat graft.

In some embodiments, the applying step includes the step of injecting DFO under dermis at the treatment site. In some embodiments, the applying step includes the step of applying DFO transdermally at the treatment site, such as by applying a transdermal delivery device to a tissue surface at the treatment site, with the DFO optionally being encapsulated in reverse micelles. In any of these embodiments, the applying step may include the step of applying DFO to the irradiated tissue in multiple discrete doses.

Some or all of the preceding embodiments may include the step of grafting fat cells at the treatment site after the applying step.

Another aspect of the invention provides a method of increasing blood perfusion in irradiated tissue. In some embodiments, the method includes the steps of applying an effective amount of DFO to the irradiated tissue at a treatment site; and increasing blood perfusion of the irradiated tissue at the treatment site.

In some embodiments, the applying step includes the step of injecting DFO under dermis at the treatment site. In some embodiments, the applying step includes the step of applying DFO transdermally at the treatment site, such as by applying a transdermal delivery device to a tissue surface at the treatment site, with the DFO optionally being encapsulated in reverse micelles. In any of these embodiments, the applying step may include the step of applying DFO to the irradiated tissue in multiple discrete doses.

Yet another aspect of the invention provides a method of increasing vascularity in irradiated tissue. In some embodiments, the method includes the steps of applying an effective amount of DFO to the irradiated tissue at a treatment site; and increasing vascularity of the irradiated tissue at the treatment site.

In some embodiments, the applying step includes the step of injecting DFO under dermis at the treatment site. In some embodiments, the applying step includes the step of applying DFO transdermally at the treatment site, such as by applying a transdermal delivery device to a tissue surface at the treatment site, with the DFO optionally being encapsulated in reverse micelles. In any of these embodiments, the applying step may include the step of applying DFO to the irradiated tissue in multiple discrete doses.

Another aspect of the invention provides a method of increasing collagen deposition in skin in irradiated tissue. In some embodiments, the method includes the steps of applying an effective amount of DFO to the irradiated tissue at a treatment site; and increasing collagen deposition of the irradiated tissue at the treatment site.

In some embodiments, the applying step includes the step of injecting DFO under dermis at the treatment site. In some embodiments, the applying step includes the step of applying DFO transdermally at the treatment site, such as by applying a transdermal delivery device to a tissue surface at the treatment site, with the DFO optionally being encapsulated in reverse micelles. In any of these embodiments, the applying step may include the step of applying DFO to the irradiated tissue in multiple discrete doses.

Still another aspect of the invention provides a method of reducing stiffness in irradiated tissue, as measured by stress/strain curves (Youngs Modulus). In some embodiments, the method includes the steps of applying an effective amount of DFO to the irradiated tissue at a treatment site; and reducing stiffness of the irradiated tissue at the treatment site.

In some embodiments, the applying step includes the step of injecting DFO under dermis at the treatment site. In some embodiments, the applying step includes the step of applying DFO transdermally at the treatment site, such as by applying a transdermal delivery device to a tissue surface at the treatment site, with the DFO optionally being encapsulated in reverse micelles. In any of these embodiments, the applying step may include the step of applying DFO to the irradiated tissue in multiple discrete doses.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6 shows a Laser Doppler Analysis following fat grafting.

FIG. 7A-E show representative H&E stained sections at 10× magnification of non-irradiated, healthy skin, irradiated skin after saline or DFO treatment, and irradiated skin after saline or DFO treatment and fat grafting. Scale bar represents 200 μm. FIG. 8 shows that a quantification of dermal thickness demonstrated significant increase following radiation, with no difference between saline or DFO treated skin. Both treatment groups demonstrated significant reduction following fat grafting ($*p<0.05$). FIGS. 9A-E show representative picrosirius red stained sections at 20× magnification demonstrating density of positive-stained collagen after irradiation and saline or DFO preconditioning, followed by fat grafting. Scale bar represents 100 µm. FIG. 10 shows that a quantification of collagen content revealed significant increase in collagen following radiation, irrespective of saline or DFO treatment. Both groups demonstrated significant reduction following fat grafting ($*p<0.05$).

DETAILED DESCRIPTION

Figure 1:
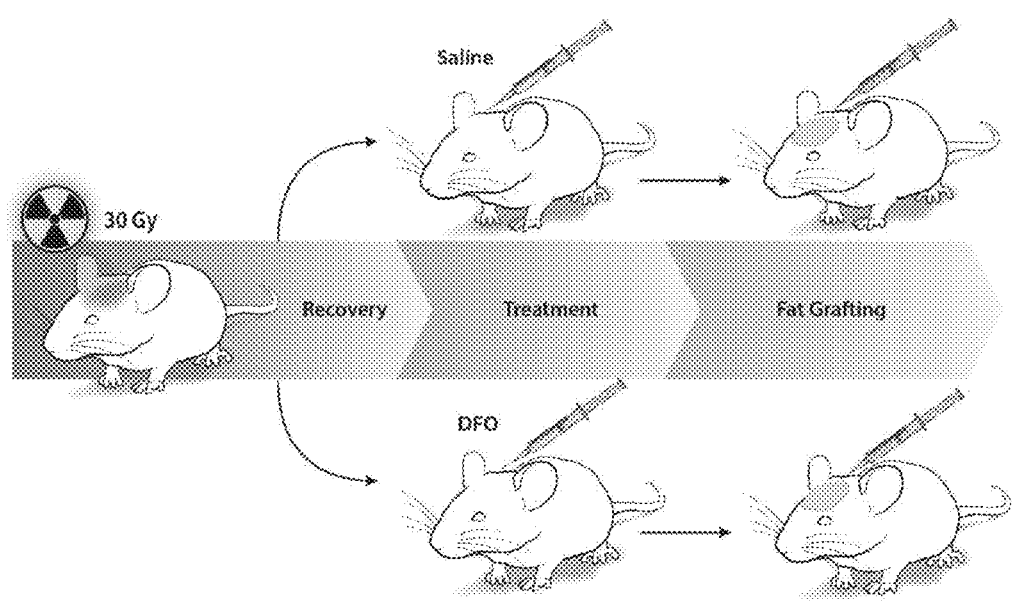
FIG. 1 shows a schematic of an irradiated tissue treatment according to this invention.

The present invention provides a method to improve fat graft outcomes. One aspect of the invention provides a method of preconditioning irradiated soft tissue site with DFO to enhance vascularity prior to implantation of a fat graft. HIF-1α is typically degraded by prolyl hydroxylase domain-containing protein 2 (PHD2). DFO, through chelation of the iron co-factor for PHD2 activity, has been shown to stabilize HIF-1α, leading to an increase in downstream angiogenic factors and recruitment of endothelial progenitor cells. This is the mechanism by which DFO has been thought to promote revascularization of ischemic skin flaps, enhance wound healing in diabetic mice, and augment callus size, mineralization, and mechanical strength at irradiated bone injury sites. Furthermore, reversal of radiation induced hypovascularity has also been appreciated with DFO treatment during mandibular distraction osteogenesis. All of these findings support the potential for DFO, through stabilization of HIF-1α and increased angiogenic gene expression, to precondition the irradiated recipient site for subsequent fat grafting.

Preconditioning the irradiated tissue at the fat graft site with DFO before implantation of the fat graft facilitates earlier revascularization of the fat graft. Histologic analysis of treated skin according to this method has revealed increased vascularity, which translates to enhanced volume retention, when fat grafts were placed into DFO preconditioned recipient sites. Interestingly, the addition of fat grafts to DFO treated irradiated tissue leads to further improvement in vascularity, even though DFO-related effects might plateau after four treatments. This suggests that alternative mechanisms may also be employed by transferred adipocytes and associated stromal cells to improve vascularity following fat grafting. Finally, the effects of DFO treatment on skin vascularity are not associated with significant changes to dermal thickness and collagen content, compared to decreased dermal thickness and collagen content following fat grafting. The architectural changes observed in the dermis with decreased collagen secondary to fat transfer may not necessarily be a result of improved vascularity alone.

In patients with radiation fibrosis and soft tissue atrophy, preconditioning tissue with serial DFO injections prior to fat grafting may be difficult logistically and not well tolerated by patients. Transdermal delivery of DFO to irradiated tissue prior to and/or after fat graft implantation may be used as an alternative to delivery of DFO via direct injection. Such an approach may also be potentially effective at preconditioning irradiated tissue for fat grafting and would likely be better tolerated by patients. Alternatively, nanoparticle formulations of DFO have also been developed, and their controlled release of DFO may similarly be employed to improve vascularity of irradiated skin. These nanoparticles may also be directly injected with fat grafts to promote earlier revascularization.

As DFO promotes expression of multiple angiogenic factors through stabilization of HIF-1α, concern may also be raised regarding its use in irradiated post-oncologic resection sites. Though no studies, to our knowledge, have demonstrated an increased risk for cancer recurrence following local administration of DFO, several reports have suggested an anti-tumor effect. Iron is necessary for oxygen transport, cell metabolism, and growth, and it is especially important in cells with active growth. Not surprisingly, iron chelators such as DFO have been found to reduce liver fibrosis, and its effect on iron metabolism has been shown to clinically reduce progression of hepatocellular carcinoma. Iron dependency has also been reported in human epidermal growth factor receptor 2 positive breast cancer cells, and multiple breast cancer cell lines have been shown to be vulnerable to iron chelation. These reports thus suggest local DFO application may not be associated with increased risk for cancer recurrence.

DFO treatment can improve radiation-induced hypovascularity, and this enhanced perfusion may improve the quality of the recipient site for fat grafting. Following DFO treatment, long-term retention of fat grafts injected into irradiated sites was significantly improved.

Reconstruction of irradiated tissue remains challenging owing to radiation induced alterations to the recipient bed. Fibroinflammatory changes and hypovascularity have been shown to impact fat graft retention, and while cell-based strategies have been shown to improve outcomes, regulatory and safety concerns have, to date, limited their translational potential. As an alternative approach, preconditioning irradiated tissue with deferoxamine improves local perfusion, which is associated with improved radiographic and histologic fat graft outcomes. Preconditioning with deferoxamine prior to fat grafting therefore holds promise for enhancing reconstruction outcomes for irradiated tissue.

EXAMPLE 1

Adult 60-day-old male Crl:NU-Fox1$^{NU}$ immunocompromised mice were used for experiments in this study. Twelve mice were treated with a total of 30 Gy external beam radiation, delivered as six fractionated doses of 5 Gy each over 12 days, followed by 5 weeks of recovery. An additional six non-irradiated mice were used as healthy controls for laser Doppler analysis (LDA) and skin analysis. Irradiated mice were divided into two treatment groups: a DFO experimental group and saline control group. Following recovery, mice underwent injection of either DFO (1 mg in 100 µl saline) or 100 µl of saline alone beneath the dermis every other day for a total of seven treatments. FIG. 1 shows a schematic of this irradiated scalp treatment.

After irradiation, fat grafting was performed on the irradiated mice. After informed consent was obtained, lipoaspirate was obtained from three healthy female donors, ages 45, 49 and 51, with no other medical co-morbidities under an approved IRB protocol #2188. Lipoaspirate was allowed to settle for 15 minutes for layers to separate by gravity sedimentation, and then oil and blood layers were removed by vacuum aspiration. The remaining fat layer was centrifuged at 1300 rcf for 3 minutes at 4° C. Any remaining oil and blood was again removed and the remaining fat was transferred into 1cc syringes for injection through a 14-gauge needle. Fat grafting was performed beneath the scalp by creating a subcutaneous tunnel with the needle and then injecting 200 µl of lipoaspirate in retrograde fashion while pulling the needle out.

Laser Doppler Analysis ("LDA") was performed to measure perfusion at the irradiated site using a Perimed PIM 3 laser Doppler perfusion imager (Datavagen, Sweden). The signal generated by the LDA, laser Doppler perfusion index (LDPI), was used for comparative purposes. LDPI is a product of the blood cell velocity and concentration and is represented by a color spectrum, with black/dark blue representing low perfusion and red representing high perfusion. LDA was performed prior to irradiation, following completion of irradiation and recovery, and then twenty-four hours following each treatment with DFO or saline. LDA was also performed every two weeks after fat grafting.

Figure 2A:
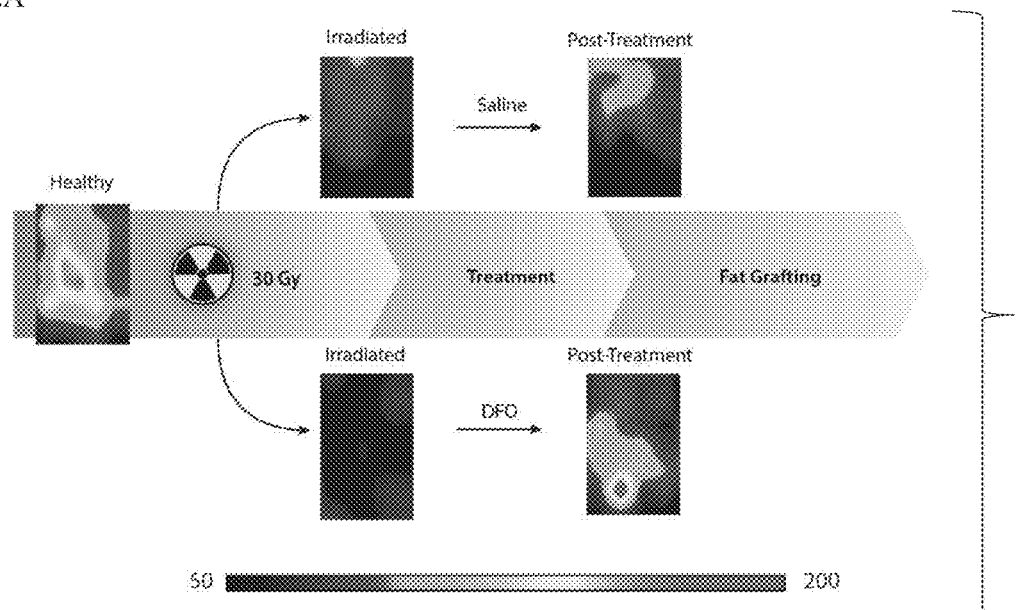
FIG. 2A shows representative photos of heat maps of mice scalps before irradiation, after irradiation, and after treatment with either saline or DFO. Darker areas represent lower perfusion and lighter areas represent higher perfusion.
Figure 2B:
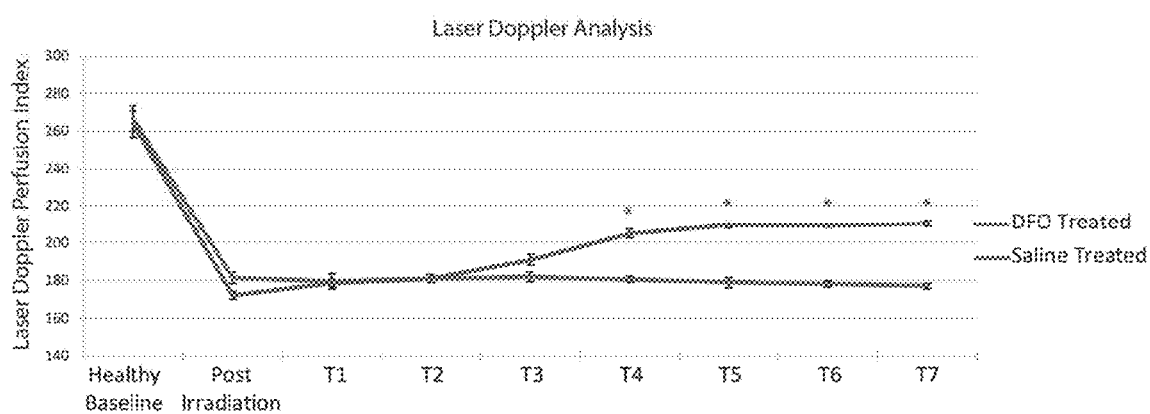
FIG. 2B shows a quantification of laser Doppler perfusion index from the irradiated mouse scalps. DFO treatments (T) caused a significance rise in perfusion after 4 treatments (T4), compared to saline injection, and plateaued after 5 treatments (T5) ($*p<0.05$).

Five images were taken of each mouse, and the average LDPI of the five images was recorded. FIG. 2A shows representative photos of heat maps of mice scalps before irradiation, after irradiation, and after treatment with either saline or DFO. Darker areas represent lower perfusion and lighter represent higher perfusion. FIG. 2B shows that quantification of laser Doppler perfusion index demonstrated a significant decrease in perfusion after irradiation. Laser Doppler analysis shows improved perfusion of irradiated tissue with DFO treatment. Laser Doppler analysis allows for the estimation of in vivo local blood perfusion in the microcirculation through frequency shifts in light that has been scattered by moving red blood cells. This facilitated longitudinal measurements in the same animal following each treatment with DFO. DFO treatments (T) (upper line in FIG. 2B) caused a significance rise in perfusion after 4 treatments (T4), compared to saline injection (lower line in FIG. 2B), and plateaued after 5 treatments (T5) (*p<0.05).

Mice were also imaged using a MicroCAT-II in vivo X-Ray micro-CT scanner (Imtek, Inc.; Knoxville, TN) two days after fat graft injection for baseline volume measurements. Fat graft volume retention was then analyzed every two weeks over a total of 8 weeks using microcomputed tomography, and images were reconstructed as three-dimensional surfaces through cubic-spline interpolation. All reconstructions were performed by a single investigator to avoid inter-observer variability.

For skin analysis, scalp skin biopsy was harvested from both treatment groups following completion of radiation and then 8 weeks following fat grafting. Specimens were fixed in 4% paraformaldehyde, processed, and embedded in paraffin for sectioning. For dermal thickness measurement, sections were stained with hematoxylin and eosin (H&E) and imaged using a Leica DM5000 B Light microscope (Leica Microsystems; Buffalo Grove, IL) at the 20× objective. Dermal measurements were made on ten stained sections from each sample. Picrosirius red staining was also performed for collagen content. Vascularity was determined with CD31 immunoflourescent staining (1:100 Ab28364; Abcam; Cambridge, MA and 1:200 AF547; Thermo Fisher Scientific; Waltham, MA) and DAPI counterstaining to visualize cell nuclei. Fluorescent images were obtained using an X-Cite 120 Fluorescence Illumination System (Lumen Dynamics Group, Inc.; Ontario, Canada) at the 20× objective. Quantification of CD31 staining was performed using ImageJ (National Institutes of Health; Bethesda, MD), with pixel-positive area per high power field measured to determine vascular density (11). Comparisons for both dermal thickness and CD31 immunofluorescent staining were also made to non-irradiated skin.

Following completion of irradiation and five-week recovery, perfusion at the scalp was noted to significantly drop from 265.23±7.01 LDPI (pre-radiation baseline) to 176.70±2.59 LDPI (FIG. 2B). However, treatment of the scalp with 1 mg of DFO every other day after radiation recovery resulted in increased LDPI, which became significant after four treatments (205.08±2.30 LDPI) (*p<0.05). No increase in LDPI measurements was noted after four treatments, though, as three additional treatments of DFO did not result in any significant increase to perfusion. In contrast, injection of saline alone resulted in no change to LDPI measurements over the entire treatment course, as shown by the lower line in FIG. 2B.

For the statistical analysis, data are presented as means±SE. Two-tailed Student's t-test was used for comparison between two groups and an analysis of variance with Tukey post-hoc test was used for multiple group comparisons. All analyses were performed using StatPlus software (Analyst-Soft, Inc., Alexandria, Va.). A value of *p<0.05 was considered significant.

Figure 3A:
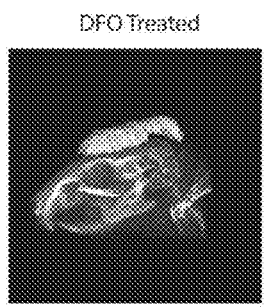
FIGS. 3A-B are representative three-dimensional reconstructions of fat grafts after eight weeks in either DFO (FIG. 3A) or saline (FIG. 3B) preconditioned irradiated scalp.
Figure 3B:
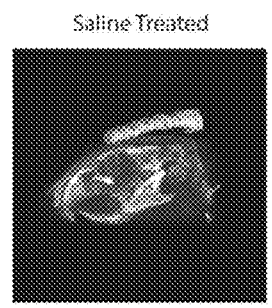
Figure 3C:
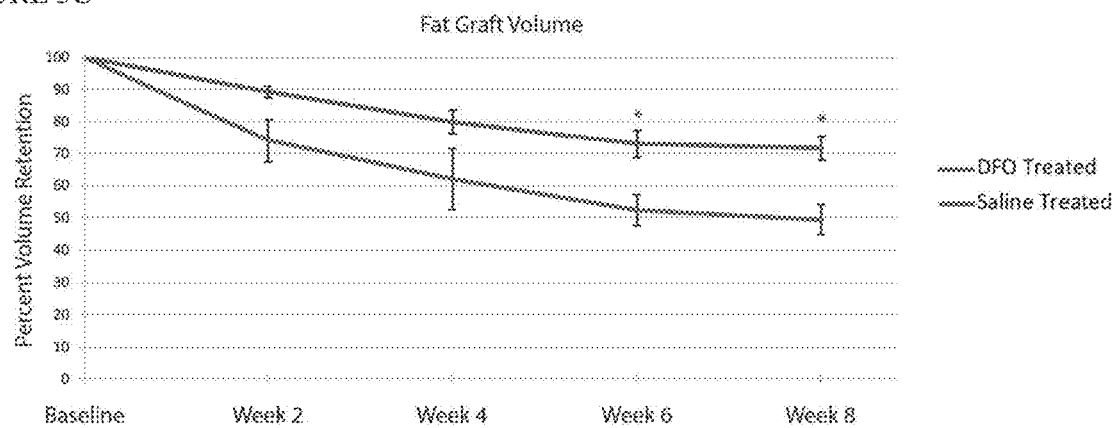
FIG. 3C shows that quantification of fat graft volumes revealed significantly increased retention in fat grafts placed into DFO treated scalp (upper line) when compared to saline treated scalp (lower line) after six and eight weeks ($*p<0.05$).

In vivo radiographic analysis of fat grafts showed DFO preconditioned irradiated mice retained more fat volume (89.24%+1.69) after two weeks compared to saline injected control mice (74.03+7.91) (FIGS. 3A-C). Fat graft volume retention was consistently greater among DFO treated mice (upper line in FIG. 3C) compared to saline control mice (lower line in FIG. 3C), and at 6 and 8 weeks, these differences were statistically significant (week 6: 73.17%±4.26 DFO vs. 52.40%±4.83 saline treated, and week 8: 71.75%±3.70 DFO vs. 49.47%+4.62 saline treated; *p<0.05).

Figure 4:
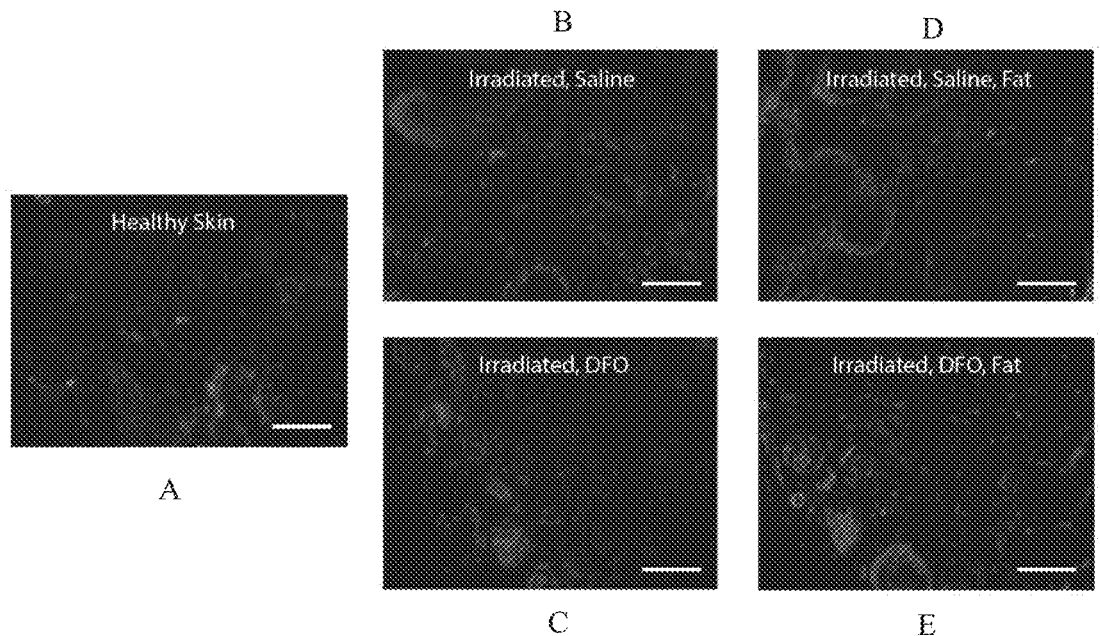
FIG. 4A-E show a histologic evaluation of irradiated scalp vascularity with representative images taken at 20× magnification of scalp skin with immunofluorescent staining for CD31 showing increased vascularity with DFO preconditioning. Scale bar represents 100 μm.

Following irradiation and saline control treatment, vascularity in skin biopsies, as demonstrated by CD31 staining, was found to be significantly lower than non-radiated healthy skin (*p<0.05) (FIG. 4A-E and FIG. 5). However, treatment of irradiated skin with DFO resulted in increased CD31 staining, though this did not reach healthy skin levels, as shown in FIG. 4A. As expected following fat grafting, skin biopsies obtained after 8 weeks also demonstrated increased CD31 staining compared to control, saline injected irradiated skin. Interestingly, slightly more CD31 staining following fat grafting was also noted with DFO preconditioned mice relative to saline control fat grafted mice, though this difference was not significant.

Figure 5:
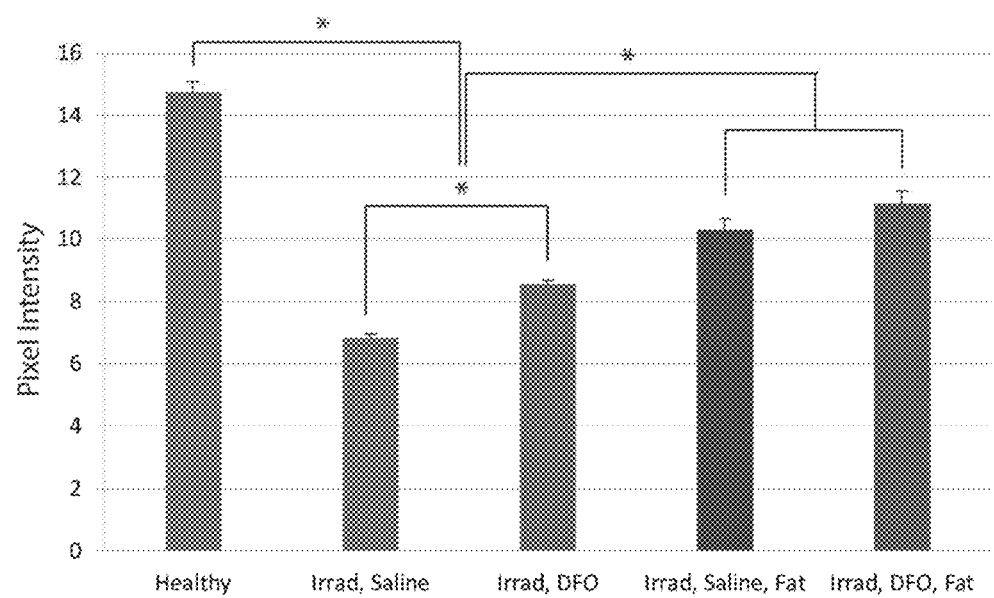
FIG. 5 shows a quantification of CD31 immunofluorescent staining revealed significant drop following irradiation. Significant improvement was noted with DFO treatment, and vascularity was further enhanced with fat grafting ($*p<0.05$).
Figure 6A:
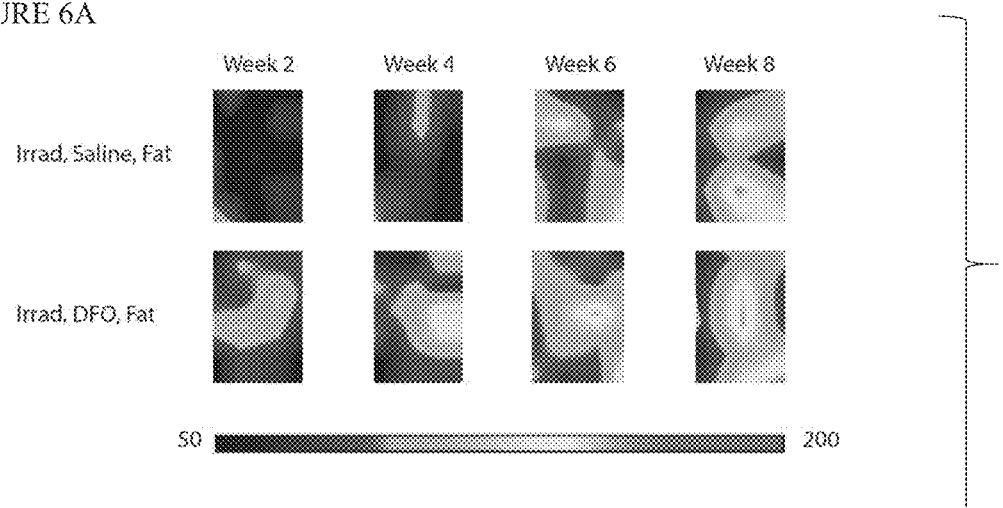
FIG. 6A shows representative LDA images of saline (top) and DFO (bottom) treated tissue scalp following fat grafting. Darker areas represent lower perfusion and lighter areas represent higher perfusion.
Figure 6B:
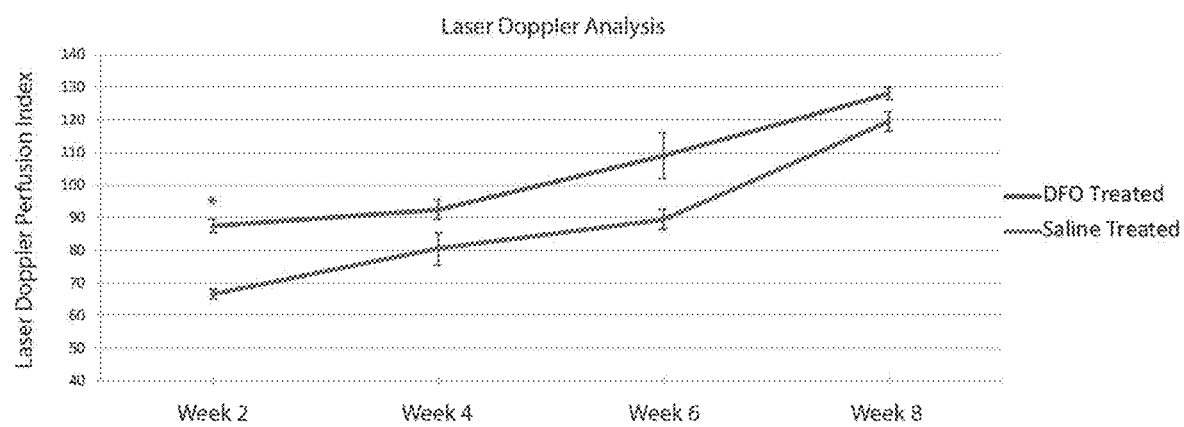
In FIG. 6B, a quantification of laser Doppler perfusion index demonstrated DFO treated scalp (upper line) had significantly higher perfusion than saline treated scalp (lower line) two weeks after fat grafting ($*p<0.05$). Both groups demonstrated increased perfusion after fat grafting with no significant difference appreciated after week 2.

Perfusion of the skin following fat grafting was also measured by LDA, and LDPI values were found to be lower than immediately following completion of DFO or saline preconditioning due to changes in three-dimensional architecture of the region of interest following placement of fat. However, two weeks following injection of fat grafts, significantly more perfusion was still noted in DFO preconditioned mice (86.33±2.00 vs. 65.72±2.02 LDPI for saline control; *p<0.05) (FIG. 5). Perfusion also continued to increase in the DFO preconditioned mice following fat grafting (upper line in FIG. 6B), but perfusion similarly increased in saline injected control mice after fat grafting (lower line in FIG. 6B), and after week 2, no significant difference on LDA was appreciated between the two groups (127.78±2.29 vs. 119.18±4.09 LDPI for DFO and saline treated mice eight weeks following grafting, respectively; p>0.05) (FIGS. 6A-B).

Figure 7:
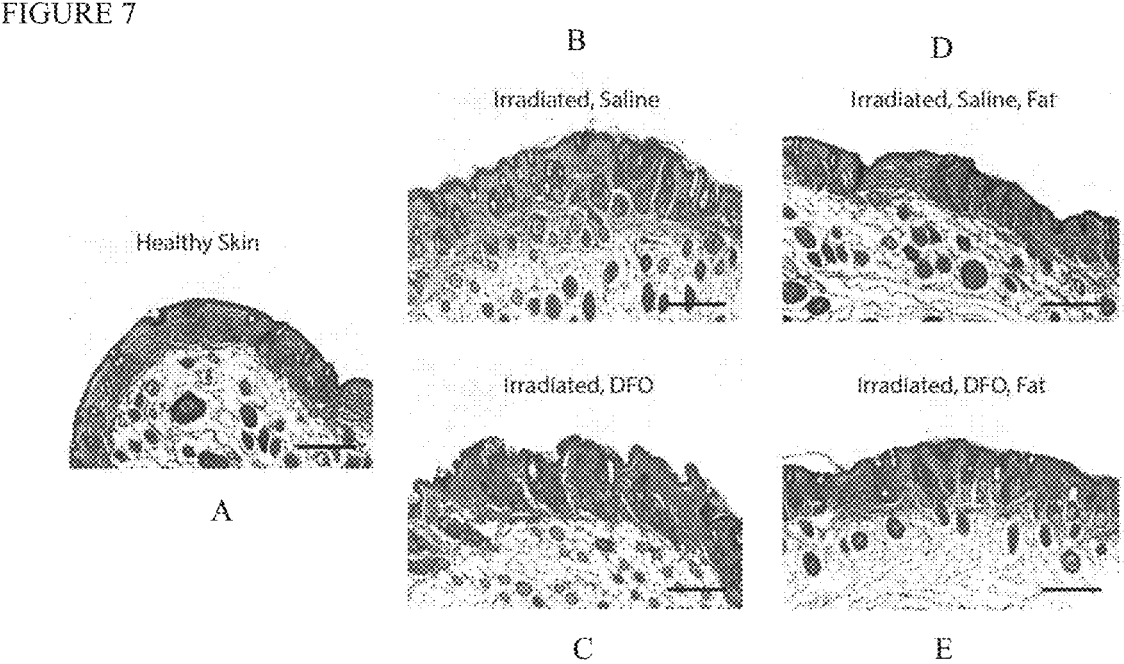
FIG. 7-10 show an evaluation of irradiated scalp histology following fat grafting.
Figure 8:
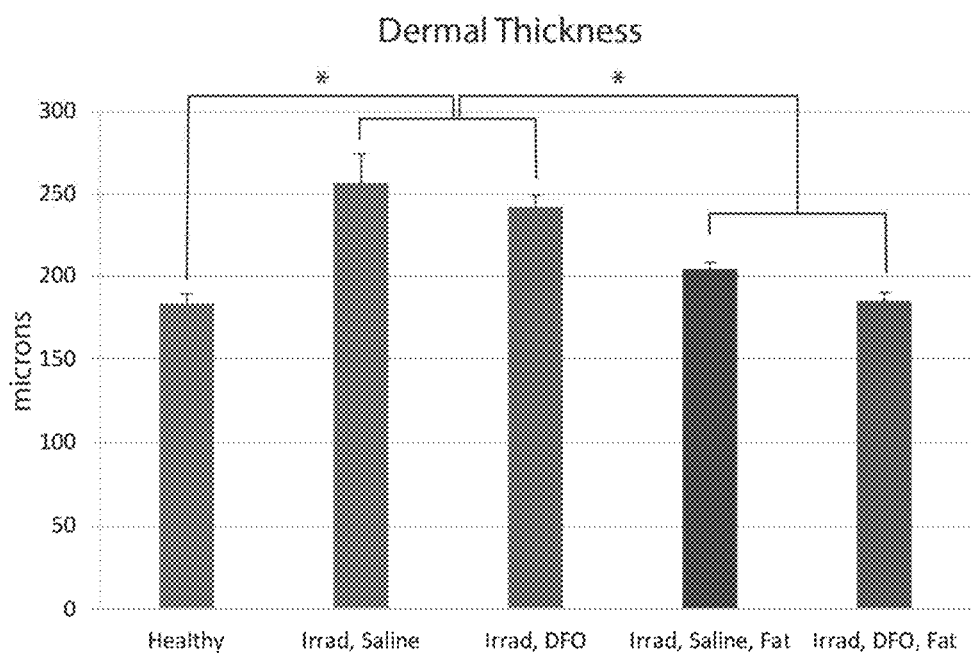
Figure 9:
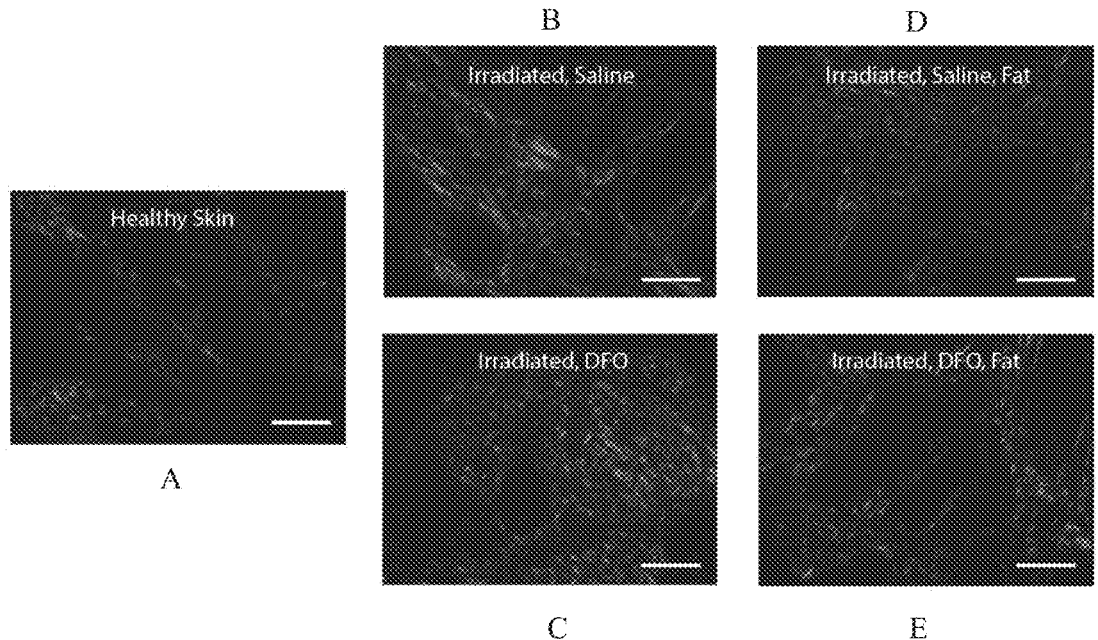
Figure 10:
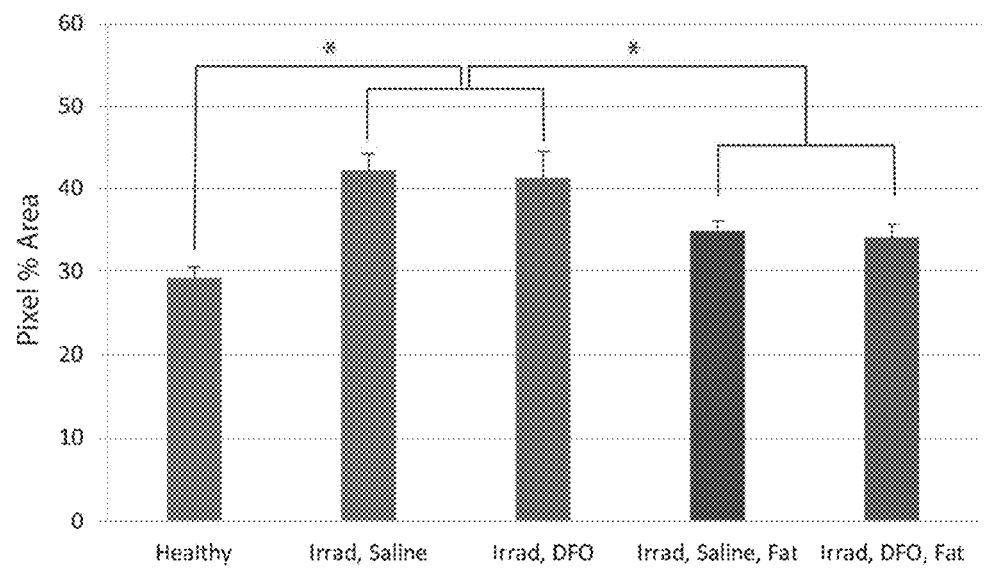

Finally, dermal thickness of irradiated skin following saline treatment was significantly greater than healthy, non-irradiated skin (*p<0.05) (FIGS. 7-8). Compared to saline injected mice (256.71±16.76 pm), DFO treatment on irradiated skin resulted in a slight decrease in dermal thickness, (242.09±7.22 pm) but this was not significantly less. However, fat grafting, whether into saline or DFO preconditioned sites, was found to significantly decrease dermal thickness, though there was no significant difference when comparing these two groups (p>0.05). Paralleling these findings, picrosirius red staining revealed significantly increased collagen content following irradiation and saline treatment (*p<0.05). DFO treatment on irradiated skin resulted in a slight decrease in collagen content which was not statistically significant. And similar to our observations with dermal thickness, fat grafting, whether into saline or DFO preconditioned sites, was found to significantly reduce collagen content (*p<0.05) (FIGS. 9-10).

Thus, local injections of DFO into irradiated hypovascular skin improved perfusion, as measured by laser Doppler analysis. Laser Doppler analysis allowed for the estimation of in vivo local blood perfusion in the microcirculation through frequency shifts in light that has been scattered by moving red blood cells. This facilitated longitudinal measurements in the same animal following each treatment with DFO. Histologic analysis of treated skin also revealed increased vascularity by CD31 staining following DFO treatment. This translated to enhanced volume retention when fat grafts were placed into DFO preconditioned recipient sites. Interestingly, the addition of fat grafts to DFO treated irradiated tissue led to further improvement in vascularity, even though DFO-related effects were seen to plateau after four treatments. This suggests that alternative mechanisms may also be employed by transferred adipocytes and associated stromal cells to improve vascularity following fat grafting. Finally, the effects of DFO treatment on skin vascularity were not found to be associated with significant changes to dermal thickness and collagen content.

EXAMPLE 2

Adult 60-day-old male Crl:NU-Fox1NU immunocompromised mice were used for experiments in this study. Twelve mice were treated with a total of 30 Gy external beam radiation, delivered as six fractionated doses of 5 Gy each every other day over 12 days, followed by one month of recovery. An additional six non-irradiated mice were used as healthy controls for laser Doppler analysis (LDA) and skin analysis. Irradiated mice were divided into two treatment groups: a DFO experimental group and a control group. Following recovery, the we applied to the irradiated scalp skin of the DFO experimental group a transdermal delivery system comprising a dry film having DFO at a concentration of 13.4% weight/weight % of film encapsulated in a reverse micelle with a non-ionic surfactant stabilized by polyvinylpyrrolidine (PVP) in an ethylcellulose matrix, cut into a ⅝ inch circle and covered by a silicon sheet of the same size. Identical transdermal delivery devices, but omitting the DFO, were applied to the irradiated scalp skin of the control group mice. The transdermal delivery systems were left in place for two days, then replaced with new devices. After irradiation and treatment with seven changes of the transdermal delivery devices, fat grafting was performed on the irradiated mice, as described in Example 1 above.

Figure 11:
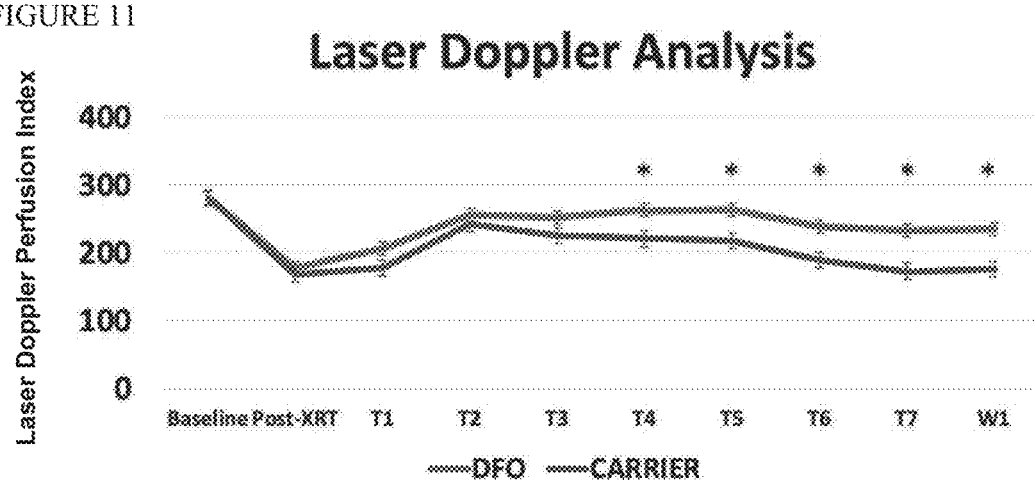
FIG. 11 shows that quantification of laser Doppler perfusion index demonstrated scalp pretreated with a DFO transdermal delivery system (upper line) had significantly higher perfusion than scalp pretreated with a transdermal delivery system lacking DFO (lower line) one week after fat grafting ($*p<0.05$).
Figure 12:
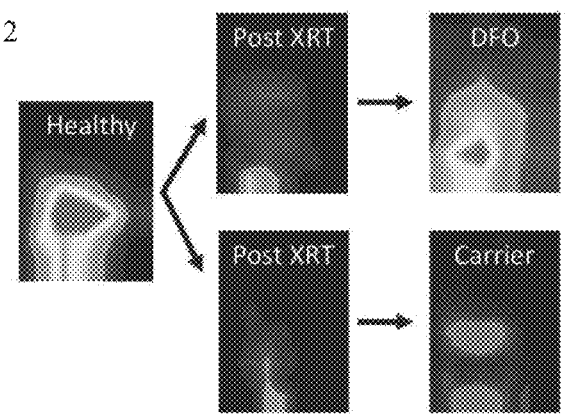
FIG. 12 shows representative LDA images of mice scalp showing perfusion in mice prior to radiation therapy (leftmost image), in an experimental group pretreated with DFO delivered by a transdermal delivery device (upper two images), and in a control group pretreated with transdermal delivery devices without DFO (lower two images) immediately after cessation of radiation therapy and one week later.

Laser Doppler Analysis ("LDA") was performed prior to and after fat grafting to measure perfusion at the irradiated site, as described above in Example 1. FIGS. 11 and 12 show that mice with the DFO transdermal delivery patches (upper line in FIG. 11) showed significant improvements in blood flow (*p<0.05) compared to mice treated with transdermal delivery devices without DFO. FIG. 11 shows that quantification of laser Doppler perfusion index demonstrated scalp pretreated with a DFO transdermal delivery system (upper line) had significantly higher perfusion than scalp pretreated with a transdermal delivery system lacking DFO (lower line) one week after fat grafting (*p<0.05). FIG. 12 shows representative LDA images of mice scalp showing perfusion in mice prior to radiation therapy (leftmost image), in an experimental group pretreated with DFO delivered by a transdermal delivery device (upper two images), and in a control group pretreated with transdermal delivery devices without DFO (lower two images) immediately after cessation of radiation therapy and one week later. Darker areas represent lower perfusion and lighter areas represent higher perfusion.

Figure 13:
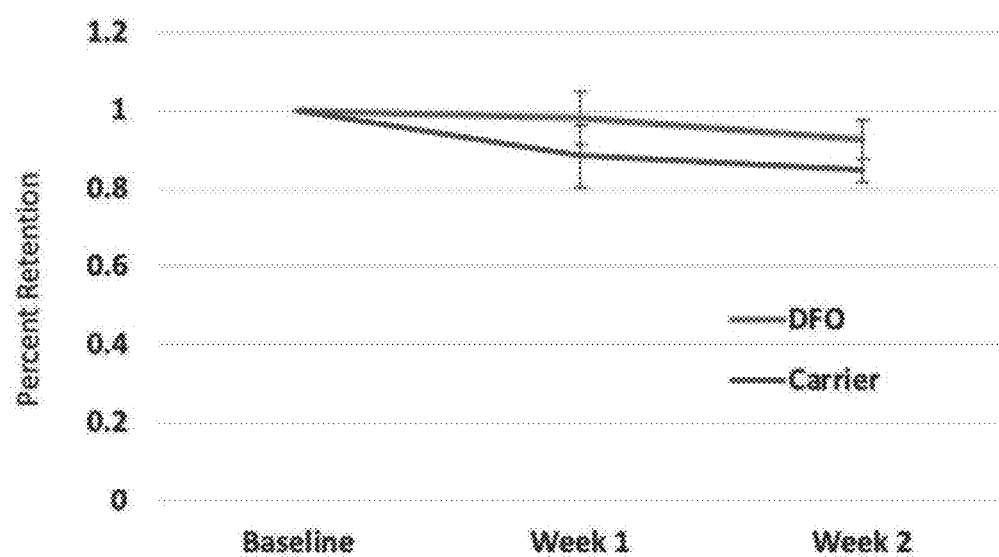
FIG. 13 shows that quantification of fat graft volumes revealed significantly increased retention in fat grafts placed into DFO treated scalp (upper line) when compared to control (no DFO) treated scalp (lower line) after one and two weeks.
Figure 14:
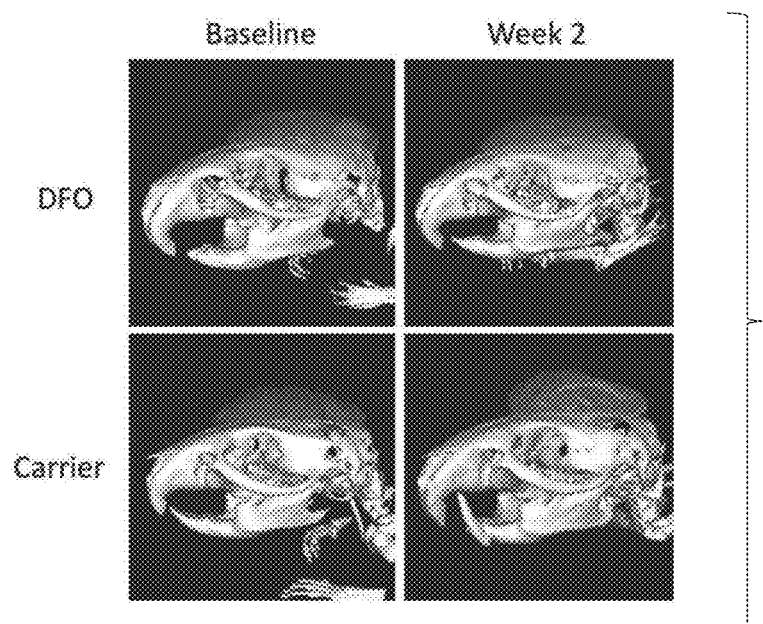
FIG. 14 shows representative three-dimensional reconstructions of fat grafts after two weeks in either DFO (upper) or control (lower) preconditioned irradiated scalp.

In vivo radiographic analysis of fat grafts showed DFO preconditioned irradiated mice retained more fat volume after two weeks compared to control mice (FIGS. 13-14). Fat graft volume retention was consistently greater among mice treated with transdermally administered DFO (upper line in FIG. 13) compared to control mice whose transdermal delivery devices lacked DFO (lower line in FIG. 13). FIG. 14 shows representative three-dimensional reconstructions of fat grafts after two weeks in either DFO (upper) or control (lower) preconditioned irradiated scalp.

Figure 15:
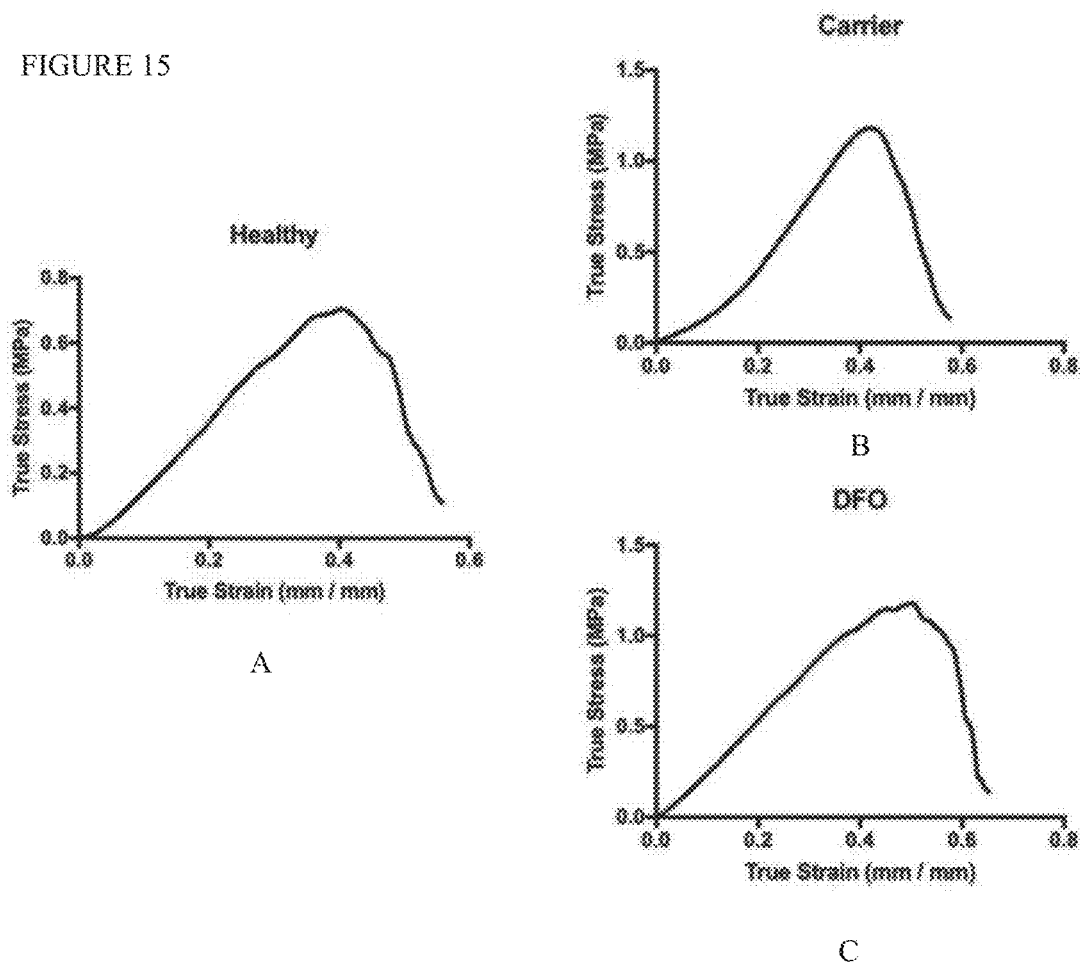
FIGS. 15A-C and 16 show skin stiffness data for healthy mice, mice treated with transdermal DFO delivery devices and mice pretreated with transdermal delivery devices without DFO.
Figure 16:
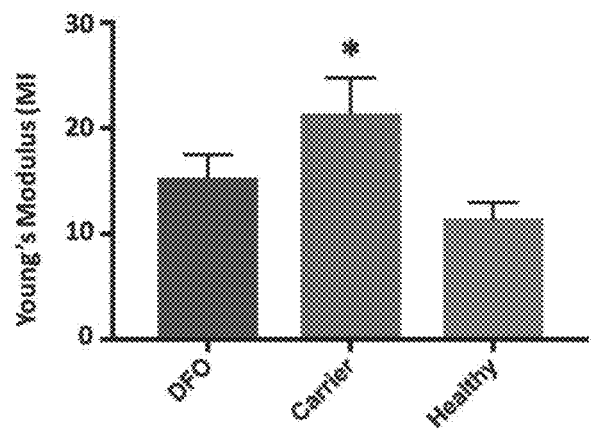

For skin analysis, scalp skin biopsy was harvested from both treatment groups following completion of radiation at the time of fat graft placement by trimming a piece of skin at the fat graft incision site. Scalp skin was also harvested from healthy mice that had not been irradiated. Skin stiffness was measured using a MTS Bionix 200 with an Interface SM-19 force transducer. Stress-strain curves were generated as shown in the figure and the Young's modulus (slope) was then calculated to figure out the stiffness. FIG. 15A shows the stress-strain curve for the healthy mice that had not been irradiated, FIG. 15B shows the stress-strain curve for the irradiated mice that had been treated with the transdermal delivery device without DFO, and FIG. 15C shows the stress-strain curve for the experimental group of irradiated mice treated with DFO via the transdermal delivery system. FIG. 16 summarizes the Young's Modulus data for the three groups. These data show that treatment of the skin with DFO after radiation therapy results in reduced skin stiffness.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of increasing blood perfusion in irradiated tissue, the method comprising:
   applying an effective amount of deferoxamine (DFO) transdermally to the irradiated tissue at a treatment site; and
   increasing blood perfusion of the irradiated tissue at the treatment site.

2. The method of claim 1 wherein the applying step comprises applying a transdermal delivery device to a tissue surface at the treatment site.

3. The method of claim 2 wherein the transdermal delivery system comprises DFO encapsulated in reverse micelles.

4. The method of claim 1 wherein the applying step comprises applying DFO to the irradiated tissue in multiple discrete doses.

* * * * *